United States Patent
Iwano et al.

(10) Patent No.: US 8,150,710 B2
(45) Date of Patent: Apr. 3, 2012

(54) MEDICAL INFORMATION SYSTEM

(75) Inventors: Kenji Iwano, Osaka (JP); Jinsei Miyazaki, Osaka (JP); Shirou Honma, Osaka (JP); Hiroyoshi Nomura, Kyoto (JP); Shunichi Nagamoto, Nara (JP)

(73) Assignee: Panasonic Corporation, Osaka (JP)

( * ) Notice: Subject to any disclaimer, the term of this patent is extended or adjusted under 35 U.S.C. 154(b) by 2149 days.

(21) Appl. No.: 10/067,843

(22) Filed: Feb. 8, 2002

(65) Prior Publication Data

US 2003/0153815 A1 Aug. 14, 2003

(51) Int. Cl.
  *G06F 19/00* (2011.01)
(52) U.S. Cl. .......... 705/3; 705/2; 705/51; 600/301; 434/236; 709/229; 726/15
(58) Field of Classification Search .......... 705/2–3, 705/51; 600/301; 709/229; 370/352; 726/15; 434/236; 380/283; 713/185
  See application file for complete search history.

(56) References Cited

U.S. PATENT DOCUMENTS

| 5,307,263 | A | * | 4/1994 | Brown | 600/301 |
| 5,339,821 | A | | 8/1994 | Fujimoto | |
| 5,822,544 | A | * | 10/1998 | Chaco et al. | 705/2 |
| 5,857,967 | A | | 1/1999 | Frid et al. | |
| 6,011,910 | A | * | 1/2000 | Chau et al. | 709/229 |
| 6,078,947 | A | | 6/2000 | Kagermeier | |
| 6,147,987 | A | * | 11/2000 | Chau et al. | 370/352 |
| 6,283,761 | B1 | * | 9/2001 | Joao | 434/236 |
| 6,944,767 | B1 | * | 9/2005 | Judson | 713/185 |
| 2001/0037384 | A1 | * | 11/2001 | Jemes et al. | 709/223 |
| 2002/0010679 | A1 | * | 1/2002 | Felsher | 705/51 |
| 2002/0066030 | A1 | * | 5/2002 | Brawn et al. | 713/201 |
| 2002/0116227 | A1 | * | 8/2002 | Dick | 705/3 |
| 2003/0039362 | A1 | * | 2/2003 | Califano et al. | 380/283 |

FOREIGN PATENT DOCUMENTS

| DE | 196 25 835 | 1/1998 |
| JP | 8-38435 | 2/1996 |
| JP | 8-275927 | 10/1996 |
| JP | 2000-29733 | 1/2000 |
| JP | 2000-250771 | 9/2000 |
| JP | 2001-167074 | 6/2001 |
| JP | 2002-24386 | 1/2002 |
| JP | 2002-32488 | 1/2002 |

OTHER PUBLICATIONS

PR Newswire. "Euclid to Monitor Health Hero Network's Internet Operations" Jan. 14, 2002. p. 1.*
Business Wire. "Spacelabs Medical, Inc. Reports First Quarter Results" Apr. 27, 1999. p. 1.*
Sutton, Neil. "Hospital offers patients Internet-based access" Aug. 2001. Technology in Government. vol. 8, Iss. 8. p. 7.*

(Continued)

*Primary Examiner* — Dilek B Cobanoglu
(74) *Attorney, Agent, or Firm* — Wenderoth, Lind & Ponack, L.L.P.

(57) ABSTRACT

A medical information system includes a patient server that retains vital information received from a patient terminal. The patient server transmits the vital information to a medical care provider server through a network. The vital information retained in the medical care provider server can then be browsed from a doctor terminal.

16 Claims, 21 Drawing Sheets

OTHER PUBLICATIONS

M2 Presswire. "ASG: ASG Technologies debuts in US market; Improves service providers' networks with first network access control & security solution; Passwerks 2.0 provides increased network efficiency, access control and security" Jun. 6, 2001. p. 1.*

Russell, Deborah and Gangemi Sr., G.T. "Computer Security Basics" Copyright 1991. O'Reilly & Associates, Inc.*

Al-Kaltham, Abdul-Rahman Ibrahim. Evaluation and Comparison of Internet Firewalls. Feb. 9, 1998.*

Taichi Nakamura et al., entitled "Human Interface of Medical Multimedia", The Journal of the Institute of Image Electronics Engineers of Japan, vol. 26, No. 3, Jul. 25, 1997, pp. 165-172.

Supplemental European Search Report issued in corresponding Application No. 02711398.4-2221 on Oct. 15, 2008.

* cited by examiner

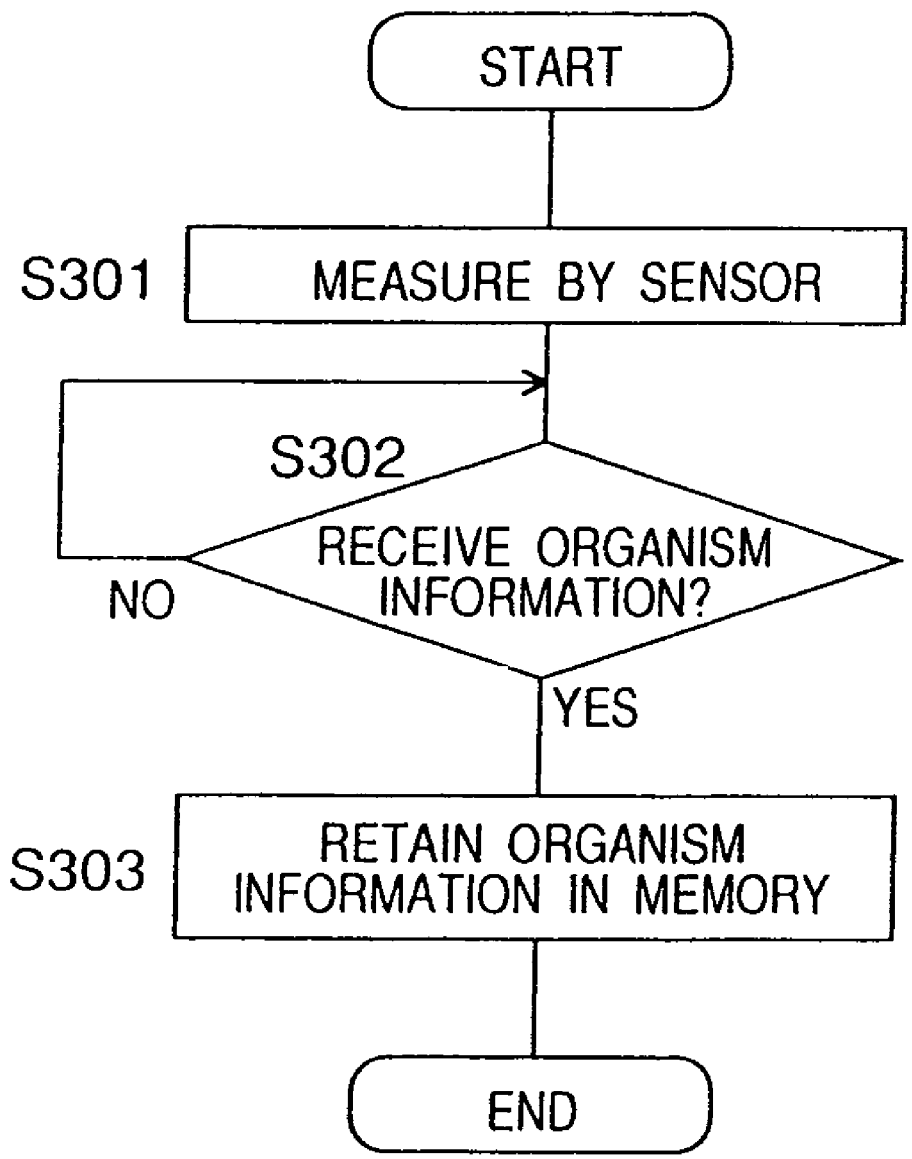

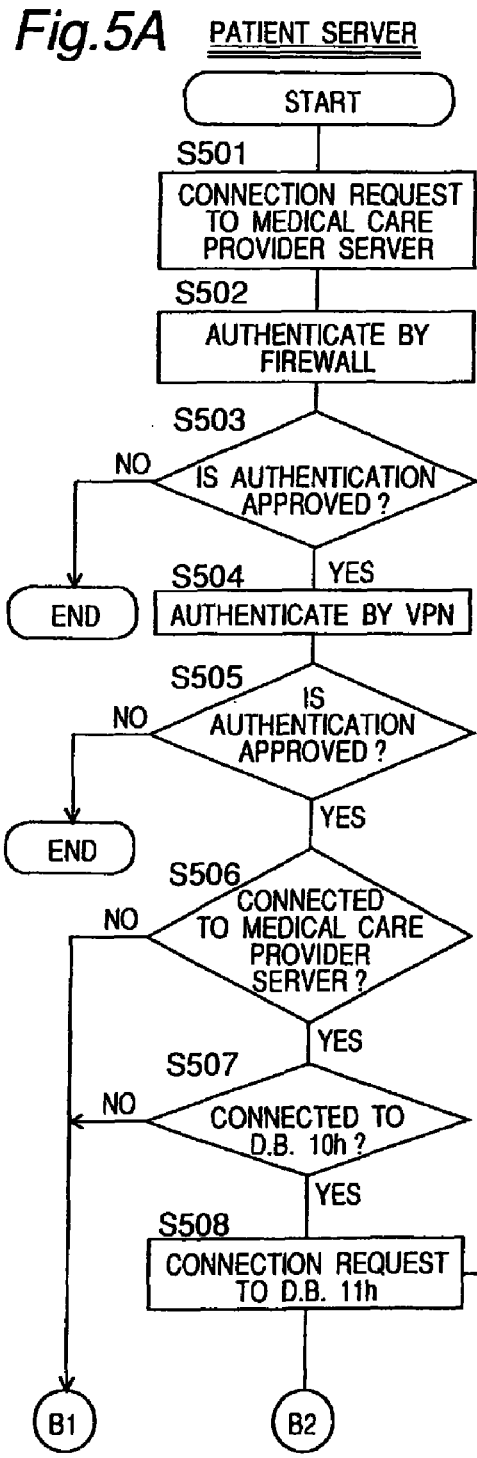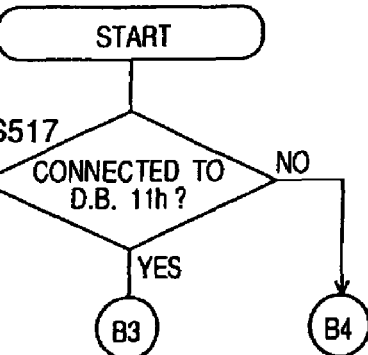
Fig.5A

Fig.10

| PATIENT ID | MEASUREMENT DATE AND TIME | MEASUREMENT VALUE (BODY WEIGHT) | TRANSMISSION FLAG |
|---|---|---|---|
| 0012 | 2001-1-30 12:34:56 | 65.75 | 0 |

| MEDICAL INQUIRY ID | CONTENTS OF MEDICAL INQUIRY | DATE AND TIME OF INQUIRY ESTABLISHMENT |
|---|---|---|
| 2 | HOW MANY TIMES DID YOU HAVE MEAL TODAY? | 2001-1-14 15:00:02 |

| PATIENT ID | CONTENTS OF MEDICAL INQUIRY | DATE AND TIME OF INQUIRY ESTABLISHMENT |
|---|---|---|
| 0012 | 2 | 2001-1-14 15:00:02 |

| PATIENT ID | DATE AND TIME OF REPLY | MEDICAL INQUIRY ID | REPLY TO MEDICAL INQUIRY | TRANSMISSION FLAG |
|---|---|---|---|---|
| 0012 | 2001-1-30 13:45:32 | 2 | 3 | 0 |

Fig.11

| PATIENT ID | MEASUREMENT DATE AND TIME | MEASUREMENT VALUE (BODY WEIGHT) |
|---|---|---|
| | | |

| MEDICAL INQUIRY ID | CONTENTS OF MEDICAL INQUIRY | DATE AND TIME OF INQUIRY ESTABLISHMENT | TRANSMISSION FLAG |
|---|---|---|---|
| 2 | HOW MANY TIMES DID YOU HAVE MEAL TODAY? | 2001-1-14 15:00:02 | 1 |

| PATIENT ID | CONTENTS OF MEDICAL INQUIRY | DATE AND TIME OF INQUIRY ESTABLISHMENT | TRANSMISSION FLAG |
|---|---|---|---|
| 0012 | 2 | 2001-1-14 15:00:02 | 1 |

| PATIENT ID | DATE AND TIME OF REPLY | MEDICAL INQUIRY ID | REPLY TO MEDICAL INQUIRY |
|---|---|---|---|
| | | | |

| PATIENT ID | PATIENT DATA (EX. NAME) |
|---|---|
| 0001 | TARO MITSUSHITA |
| ... | ... |
| 0012 | HANAKO MATUSHITA |

MEDICAL INFORMATION SYSTEM

BACKGROUND OF THE INVENTION

1. Field of the Invention

The present invention relates to a medical information system which is adapted to home health care.

2. Description of the Related Art

Medical information systems have recently been provided in which vital information of home care patients is collected through a network, and the vital information collected through the network can be browsed. For instance, a system disclosed in Japanese laid-open patent publication No. 8-38435 has a plurality of patient terminals for transmitting measured vital data, a single server for storing and managing the vital data received from these patient terminals, and a plurality of doctor terminals for obtaining or browsing the vital information retained in the single server.

However, this system provided with the single server has the following problems.

First, load to the server for data correction processes is increased with an increasing number of the patient terminals. The loads to the server at data browsing processes are also increased with an increasing number of the doctor terminals. These increases of the loads to the server cause a delay in response time and a decrease in a transmission rate. Especially, extremely heavy loads to the server may cause the data collection from the patient terminals and the data browsing from the doctor terminals to be impossible.

Second, while the sever is downed (taken offline and/or shut down) to modify a program installed therein so as to adapt the program to changes in specification or the addition of a patient terminal, the data browsing from the doctor terminals becomes impossible. Similarly, in the case of changes in specification or the addition of a doctor terminal, the data collection from the patient terminals becomes impossible due to the server being taken down to change the program.

Third, the single server can not satisfy both requirements from a system administrator and requirements that are inconsistent with the system administrator's requirement from medical institutions such as hospitals that are users of the doctor terminals. Specifically, the system administrator generally demands to hold the server so as to operate and manage it. Contrary to this, the medical institutions demand to hold the server so as to make it able to use the vital data collected from the patient terminals in other medical information systems such as an electronic chart system.

Fourth, the single server has a low level of security protections. Specifically, third parties with bad faith may access the vital information by using the patient terminal without proper authentication.

SUMMARY OF THE INVENTION

With consideration to the problems regarding the above-mentioned conventional medical information systems, objects of the present invention are to reduce the loads to the server, enhance flexibility of the system, and improve security properties.

Therefore, a first aspect of the present invention provides a medical information system comprising: a patient server that can receive vital information, retain the received vital information, and transmit the retained vital information; and a medical care provider server connected to the patient server through a first network. The medical care provider server is capable of retaining the vital information received from the patient server through the first network and allowing the retained vital information to be browsed or viewed.

The medical information system further comprises a patient terminal connected to the patient server through a second network, where the patient terminal is capable of transmitting the vital information to the patient server through the second network. The medical information system also comprises a doctor terminal connected to the medical care provider server through a third network, where the doctor terminal is capable of browsing the vital information retained in the medical care provider server through the third network.

In the medical information system according to the first aspect of the invention, the patient server processes collection of the vital information from the patient terminal, whereas the medical care provider server processes browsing of the vital information by the doctor terminal. In other words, in the medical information system, the processes are decentralized by concurrent processes in the two servers, thereby reducing loads to each of the respective servers. Thus, response time is shortened, resulting in an improvement of communication speed. Further, stability of the system is improved by reducing the loads to the patient server and the medical care provider server. This enables the collection of the vital information form the patient terminal and the browsing of the vital information by the doctor terminal to always be executed in a stable manner.

The patient terminal is connected to the patient server, whereas the doctor terminal is connected to the medical care provider server. Accordingly, when a server program is modified so as to adapt the program to changes in specification or the addition of another patient terminal, only the patient server needs to be downed, whereas the browsing of the vital information retained in the medical care provider server by the doctor terminal can be continued. Conversely, when the server program is modified so as to adapt the program to changes in specification or the addition of another doctor terminal, only the medical care provider server needs to be downed, whereas the collection of the vital information by the patient server can be continued.

The system administrator can hold the patient server to operate and manage it, thereby simplifying the maintenance and operation of the data. On the other hand, the medical institute can hold the medical care provider server so as to use the vital information retained in the medical care provider server for other medical information systems such as the electronic chart system. As a result, the medical information system according to the first aspect of the present invention has high flexibility.

Specifically, the patient terminal is provided with a sensor for measuring vital data, and the vital information includes a measured value by the sensor.

The medical care provider server can transmit the inquiry received from the doctor terminal to the patient server through the first network. The patient server may transmit the inquiry received from the medical care provider server to the patient terminal through the second network. The vital information transmitted from the patient terminal to the patient server through the second network may include a reply to the inquiry transmitted to the patient terminal.

Preferably, the medical information system includes a first unauthorized access prevention section provided in the first network, a second unauthorized access prevention section provided in the second network and a third unauthorized access prevention section provided in the third network. The first and third unauthorized access prevention sections preferably have higher security levels than that of the second unauthorized access prevention section.

For instance, the first unauthorized access prevention section is provided with a firewall and a virtual private network, the second unauthorized access prevention section is provided with a remote access server, and the third unauthorized access prevention section is provided with a terminal authentication server.

The patient server only can be accessed directly from the patient terminal through the second network. Further, the first unauthorized access prevention section provided in the first network providing communicating between the patient server and the medical care provider server has a higher security level than that of the second unauthorized access prevention section. Accordingly, unauthorized access from the patient server to the vital information retained in the medical care provider server can be prevented. Also, the lower security level of the second unauthorized access prevention section than those of the first and third unauthorized access prevention sections ensures a convenient connection from the patient terminal to the patient server. The high security level of the third network for connecting the doctor terminal and the care provider server prevents unauthorized access directly to the medical care server. As a result, the medical information system according to the first aspect of the present invention has very high level of security.

The patient server and the medical care provider server may be respectively clustered. Clustering of the patient server and the medical care provider server makes it possible to realize further decentralization of the loads to the servers. The clustering also improves fault tolerance and makes it possible to realize a system that remains operable 24 hours a day.

A second aspect of the invention provides a medical information system comprising: a plurality of patient servers that can receive vital information, retain the received vital information, and transmit the retained vital information; a medical care provider server connected to the patient servers through a first network, where the medical care provider server is capable of retaining the vital information received from the patient servers through the first network and allowing the retained vital information to be browsed; a plurality of patient terminals respectively connected to the patient server through a second network, where the patient terminals are capable of transmitting the vital information to the patient server through the second network; and a doctor terminal connected to the medical care provider server through a third network, where the doctor terminal is capable of browsing the vital information retained in the medical care provider server through the third network.

In the medical information system according to the second aspect of the present invention, when a server program is modified so as to adapt the program to change in specification or the addition of patient terminals connected to one of the plurality of patient servers, only the corresponding patient server needs to be downed. The other patient servers can continue to collect the vital information form the patient terminals connected thereto.

A third aspect of the present invention provides a medical information system comprising: a patient server that can receive vital information, retain the received vital information, and transmit the retained vital information; a plurality of medical care provider servers respectively connected to the patient server through a first network, where the medical care provider servers are capable of retaining the vital information received from the patient server through the first network and allowing the retained vital information to be browsed; a patient terminal connected to the patient server through a second network, where the patient terminal is capable of transmitting the vital information to the patient server through the second network; and a plurality of doctor terminals respectively connected to the medical care provider servers through a third network, where the doctor terminals are capable of browsing the vital information retained in the medical care provider servers through the third network.

In the medical information system according to the third aspect of the present invention, the plurality of medical care provider servers can be respectively held and managed by corresponding medical institutes. Accordingly, each of the medical institutes can retain the vital information in its medical care provider server for long term. Further, views at doctor terminals when the vital information is browsed can be customized in accordance with each of the medical institutes.

BRIEF DESCRIPTION OF THE DRAWINGS

Further objects and advantages of the present invention will become clear from the following description when taken in conjunction with the preferred embodiments thereof with reference to the accompanying drawings, in which:

FIG. 3 is a flow chart for explaining measurement of vital information;

FIGS. 5A and 5B are respectively a flow chart for explaining transmission of the vital information from the patient server to a medical care provider server;

FIG. 10 is a schematic view showing an example of a data structure of the patient server;

FIG. 11 is a schematic view showing an example of a data structure of the medical care provider server;

DETAILED DESCRIPTION OF THE PREFERRED EMBODIMENTS

First Embodiment

Figure 1:
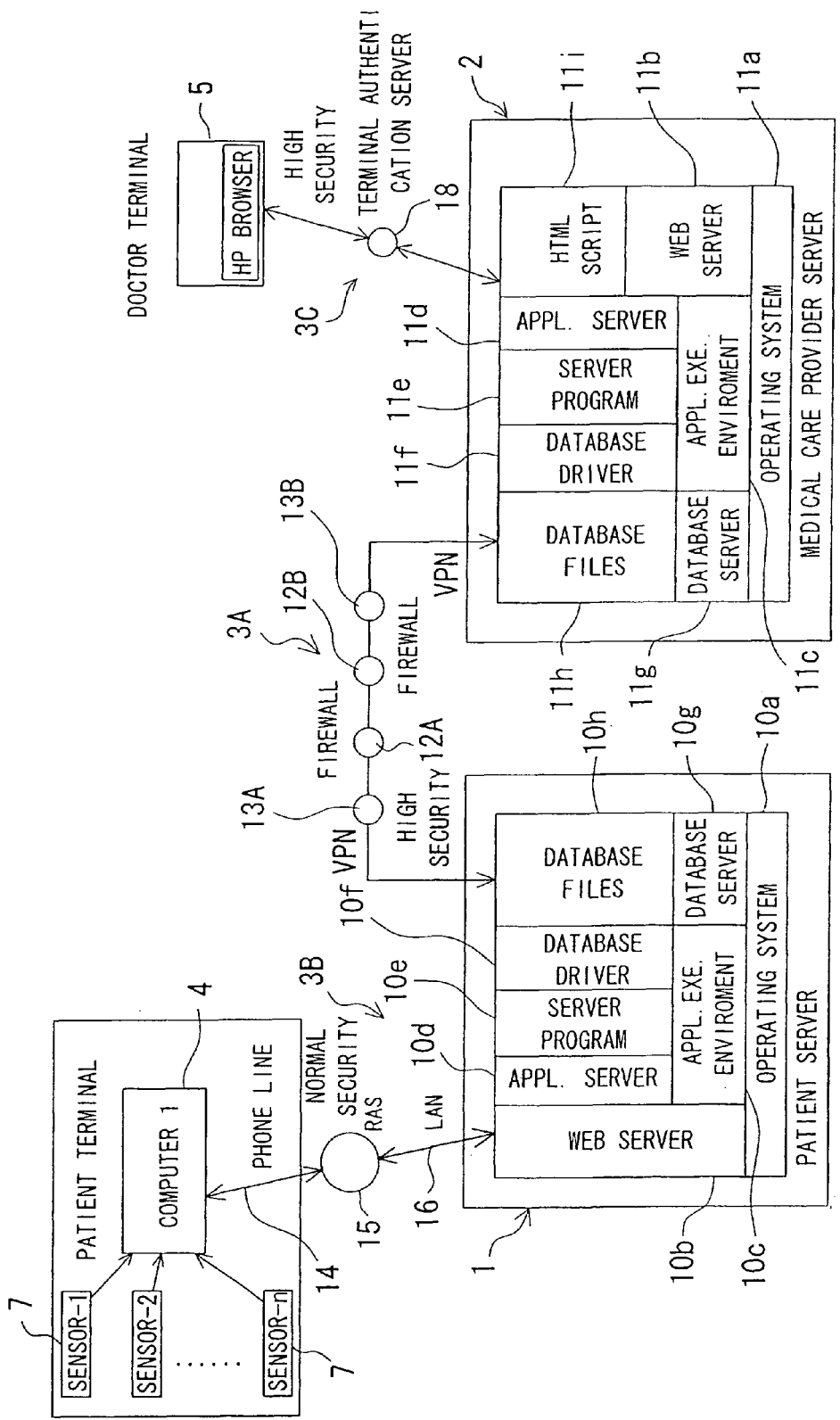
FIG. 1 is a block diagram showing a medial information system according to a first embodiment of the present invention.
Figure 2:
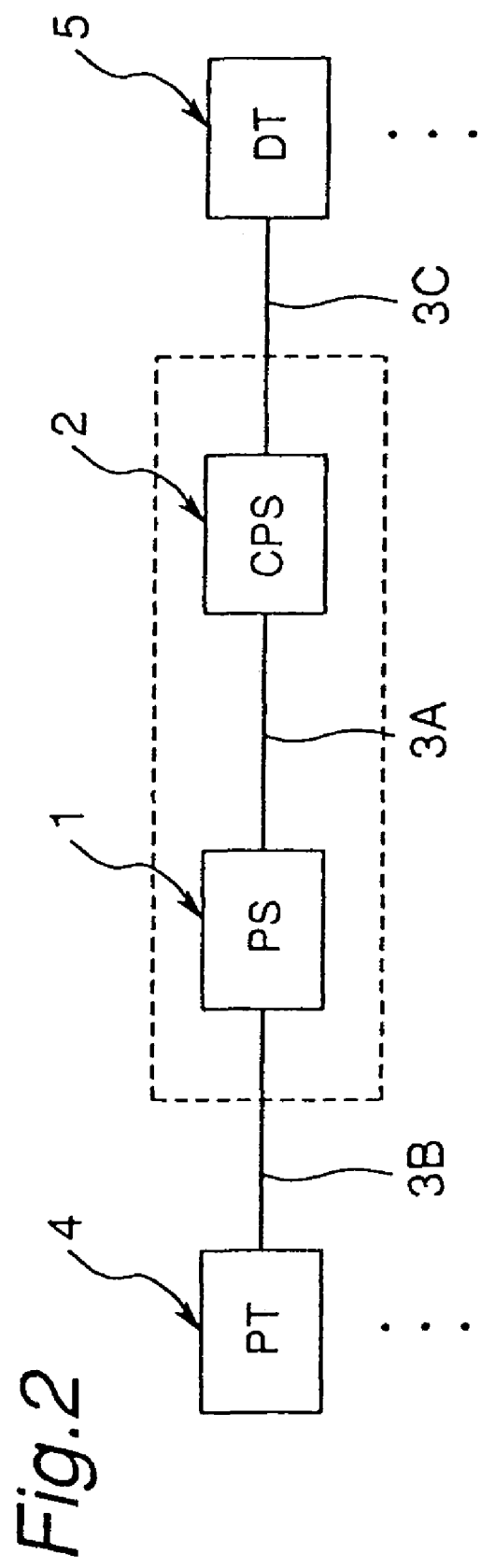
FIG. 2 is a schematic block diagram showing the medical information system according to the first embodiment of the present invention.

As illustrated in FIGS. 1 and 2, a medical information system according to a first embodiment of the present invention is provided with a patient server (PS) 1 and a medical care provider server (CPS) 2 that are connected with each other through a first network 3A. Further, this medical information system is provided with a plurality of patient terminals (PT) 4 respectively connected to the patient server 1 through a second network 3B, and a plurality of doctor terminals (DT) 5 respectively connected to the medical care provider server 2 through a third network 3C.

In outline, vital data is transmitted from the patient terminal 4 to the patient server 1 through the second network 3B. As will be described later, the vital data includes a measurement value and a reply to a medical inquiry (inquiry). The patient server 1 temporally retains the vital data received from the patient terminals 4. The patient server 1 transmits the vital data retained therein to the medical care provider server 2 through the first network 3A in accordance with a request from the medical care provider server 2. The medical care provider server 2 retains the vital information received from the patient server 1. The data stored in the medical care provider server 2 can be browsed or viewed from one or more of the doctor terminals 5 through the third network 3C.

The patient terminal 4, for instance, consists of a personal computer to which a plurality of sensors 7 for measuring the vital data of patients are connected. These sensors may, include, for example, a hemadynamometer and a scale.

A software construction of the patient server 1 will now be described. First, the patient server 1 is provided with Web server software 10b which runs on an operating system 10a. For example, Windows 2000® from Microsoft® may be adopted as the operating system 10a. Further, Internet Information Server® (IIS), for example, may be adopted as the Web server software 10b. Furthermore, application server software 10d, a server program 10e, and a database driver 10f are operated on an application execution environment 10c. Java Virtual Machine® (JVM) from Javasoft®, for example, can be adopted as the application execution environment 10c. Further, JRUN® from Macromedia® can be adopted as the application server software 10d, Furthermore, JDBC® from Inet® can be adopted as the database driver 10f. According to commands from the server program 10e, the database driver 10f manipulates database files 10h by using a database server 10g as an interface.

Similar to the patient server 1, the medical care provider server 2 is provided with web server software 11b (e.g. IIS from Microsoft®) operated on an operating system 11a (e.g. Windows 2000® from Microsoft®). Further, application server software 11d (e.g. JRUN® from Macromedia®), a server program 11e, and a database driver 11f (e.g. JDBC® from Inet®) are operated on an application execution environment 11c (e.g. JVM from Jabasoft). The database driver 11f manipulates database files 11h by using a database server 11g as an interface. Furthermore, the medical care provider server 2 is provided with HTML and a scrip 11i manipulated on the Web server software 11b.

The doctor terminal 5 consists of, for example, a normal personal computer. As will be described later, the doctor terminal 5 is provided with browser software for communicating with the medical care provider server 2.

The first network 3A for connecting the patient server 1, and the medical care provider server 2 is provided with a firewall 12A and a virtual private network (VPN) 13A for the patient server 1 as well as a firewall 12B and a VPN 13B for the medical care provider server 2.

The second network 3B for connecting each of the patient terminals 4 and the patient server 1 to allow communication therebetween is provided with a remote access server (RAS) 15 connected to each of the patient terminals 4 through a phone line 14 and a local area network 16.

The third network 3C for connecting each of the doctor terminals 5 and the medical care provider server 2 to allow communication therebetween is provided with a terminal authentication server 18.

The operation of the medical information system will be described below with reference to flow charts in FIGS. 3 to 9B.

First, measurement of the vital data in the patient terminal 4 will be described with reference to FIG. 3. At step S301, the sensor 7 for measuring performs measurement of the vital data such as blood pressure, body temperature, or body weight. Then, if the patient terminal 4 receives the vital data at step S302, the patent terminal 4 then retains the data in its memory at step S303.

Figure 4A:
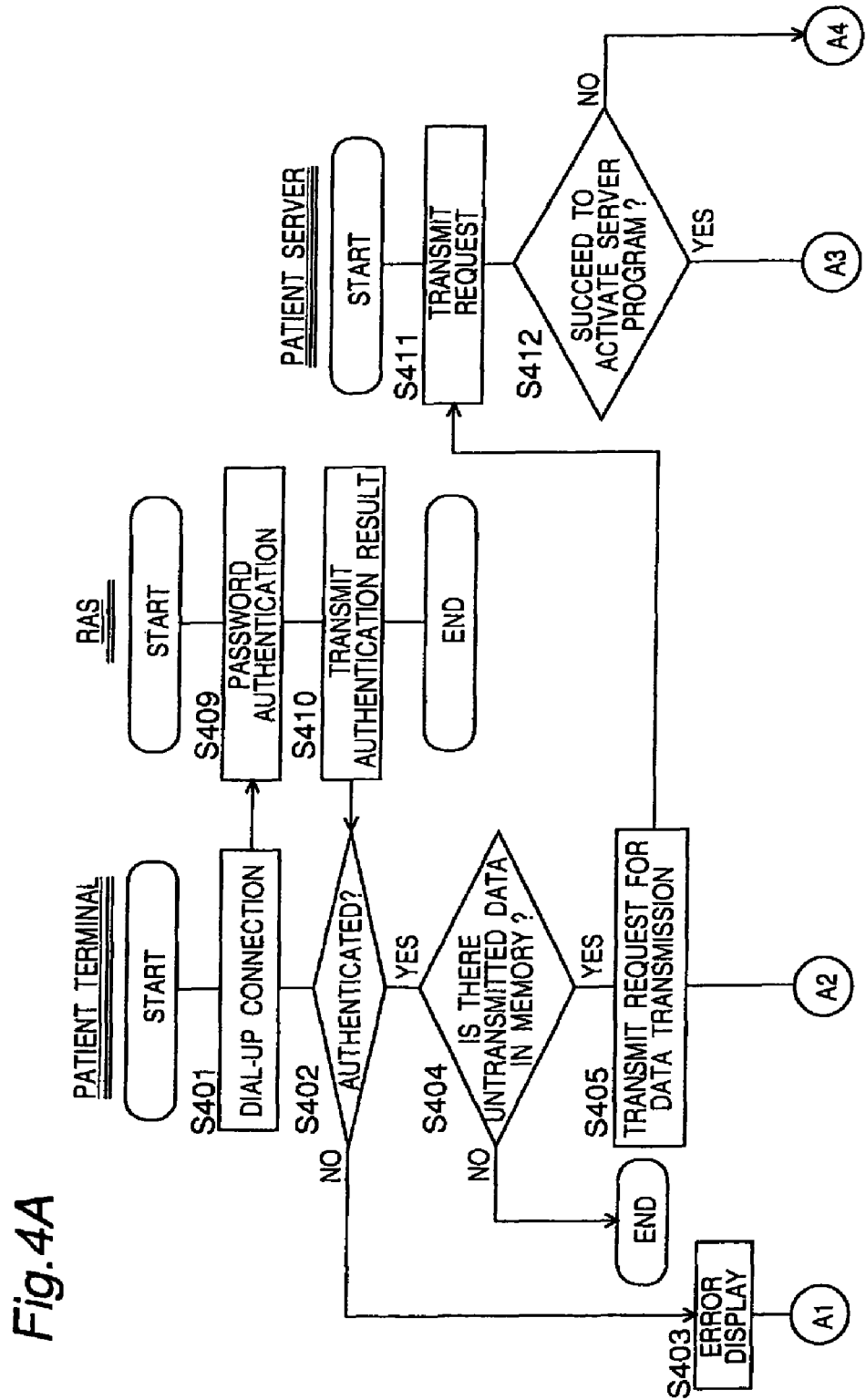
FIGS. 4A and 4A are respectively a flow chart for explaining transmission of the vital information from a patient terminal to a patient server.
Figure 4B:
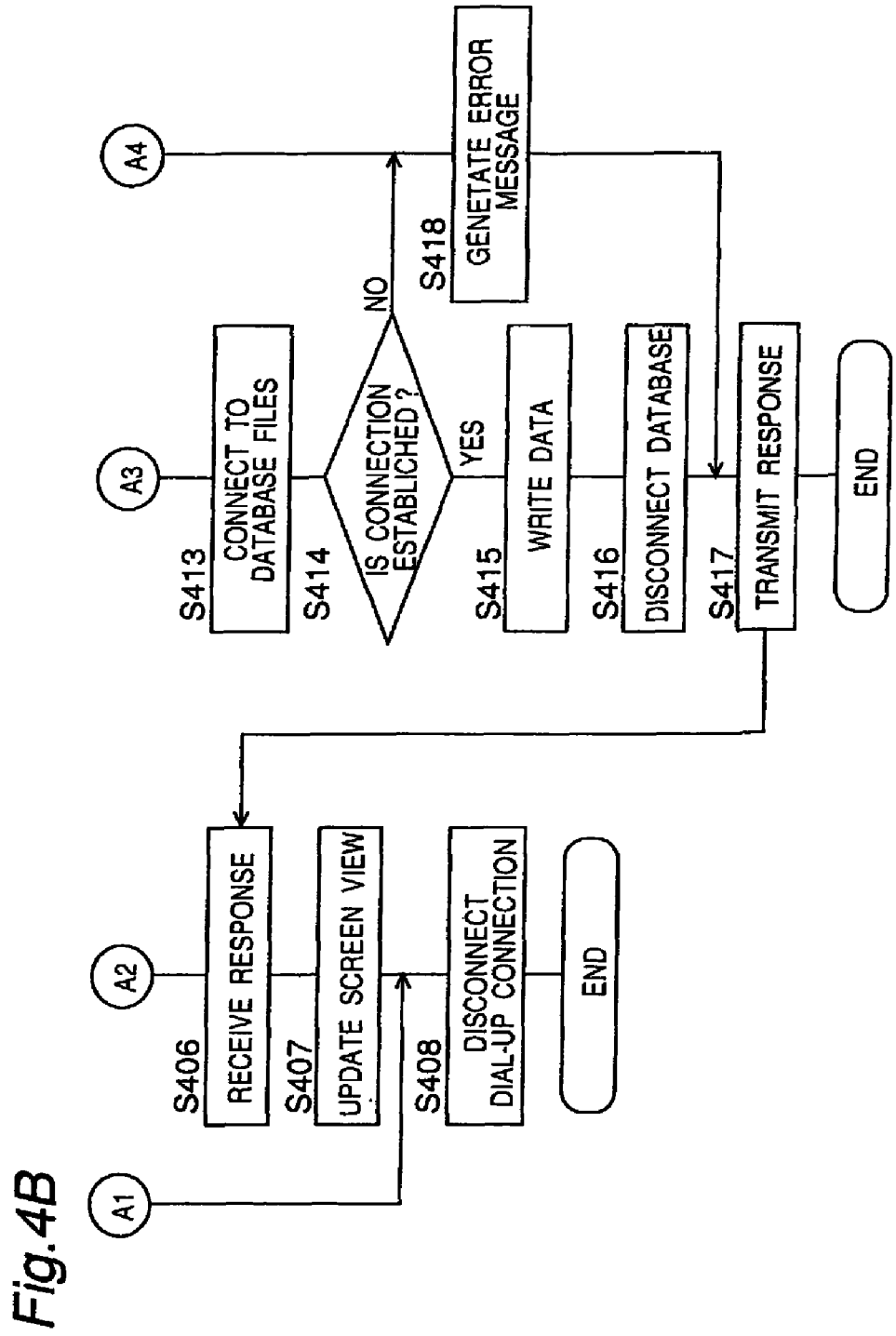

FIGS. 4A and 4B illustrate processes that are performed until the vital data retained in the memory of the patient terminal 4 is transmitted to the patient server 1. In addition to above-mentioned measurement value such as the blood pressure or body temperature, the vital data retained in the memory of the patient terminal 4 includes the reply to one or more inquiries that have been transmitted to the patient server 4 from the doctor terminal 5 through the medical care provider server 2 and the patient server 1. First, at step S401, the patient terminal 4 requires access to the RAS 15 by means of a dial-up connection through the phone line 14. The RAS 15 performs authentication of the patient terminal 4 that is requiring the access by means of a password at step S409, and then transmits a result of the authentication to the patient terminal 4 at step S410. If the authentication has been denied at step S402, then the patient server 4 performs an error display at step S403 and disconnects the dial-up connection at step S408. On the other hand, if the authentication has been approved at step S402, the patient terminal 4 checks whether or not there is vital data in its memory that has not yet been transmitted. If there exists any vital data that has not yet been transmitted, then the patient terminal 4 transmits a request for data transmission to the patient server 1 at step S405. After receiving the request at step S411, in the case where activation of the server program 10e succeeds at step S412, the patient server 1 performs connection to the database files 10h at step S413. Further, in the case where the connection to the database files 10h has succeeded at step S414, the patient server 1 writes the data to the database files 10h at step S415 followed by disconnection of the database files 10h at step S416. On the other hand, in the case where the activation of the server program 10e has failed at step S412, an error message is generated at step S418. Lastly, the patient server 1 transmits a response to the patient terminal 4 at step S417.

After receiving the response from the patient server 1 at step S406 and updating a screen view at step S407, the patient terminal 4 disconnects the dial-up connection at step S408.

Figure 5B:
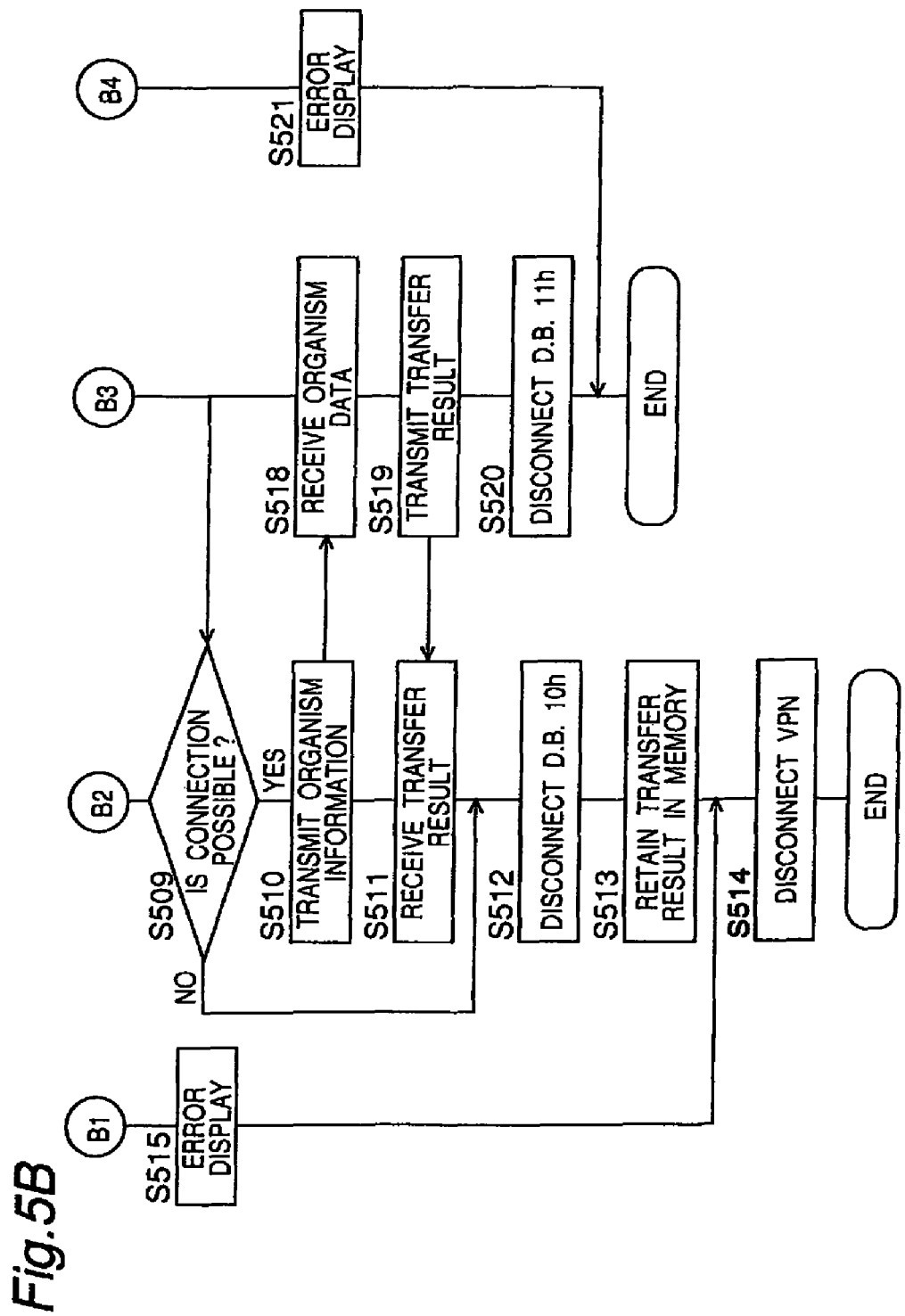

FIGS. 5A and 5B illustrate processes that are performed until the vital data has been transmitted from the patient server 1 to the medical care provider server 2.

First, subsequent to transmission of a connection request from the patient server 1 to the medical care server 2 at step S501, the firewall 12B for the medical care provider server 2 performs authentication at step S502. If the authentication by the firewall 12B has been approved at step S503, then the VPN 13B for the medical care provider server 2 performs further authentication at step S504. In the case where the authentication by the VPN 13B has been approved at step S505, where connection to the medical care provider server 4 is determined to be possible at step S506, and where it is determined that the patient server 1 can be connected to the database files 10*h* thereof at step S507, the patient server 1 requests the medical care provider server 2 to connect to the database files 11*h*. On the other hand, in the case where the connection to the medical care provider server 2 is determined to be impossible at step S506, or where the connection to the database files 11*h* is determined to be impossible at step S507, the patient server 1 performs the error display at step S515.

If the connection to the database files 11*h* is determined to be possible at step S517, then the medical care provider server 2 informs an existence of the possibility to the patient server 1. On the other hand, if the connection to the database files 11*h* is determined to be impossible at step S517, the medical care provider server 2 performs the error display.

If the patient server 1 has received the notification of the possibility for connection to the database files 11*h* from the medical care provider server 2 at step S509, the patient server transmits the vital data to the medical care provider server 2 at step S510. The transmitted vital data is received by the medical care provider server 2 at step S518, and is then retained in the database files 11*h*. Next, the medical care provider server 2 transmits a transfer result to the patient server 1 at step S519 and disconnects the connection to the database files 11*h* at step S520.

After receiving the transfer result from the medical care provider server 2 at step S511, the patient server 1 disconnects the connection to the database files 10*h* at step S512 and stores the transfer result in the memory. Then, the patient server 1 disconnects the connection to the VPN 13B.

Figure 6A:
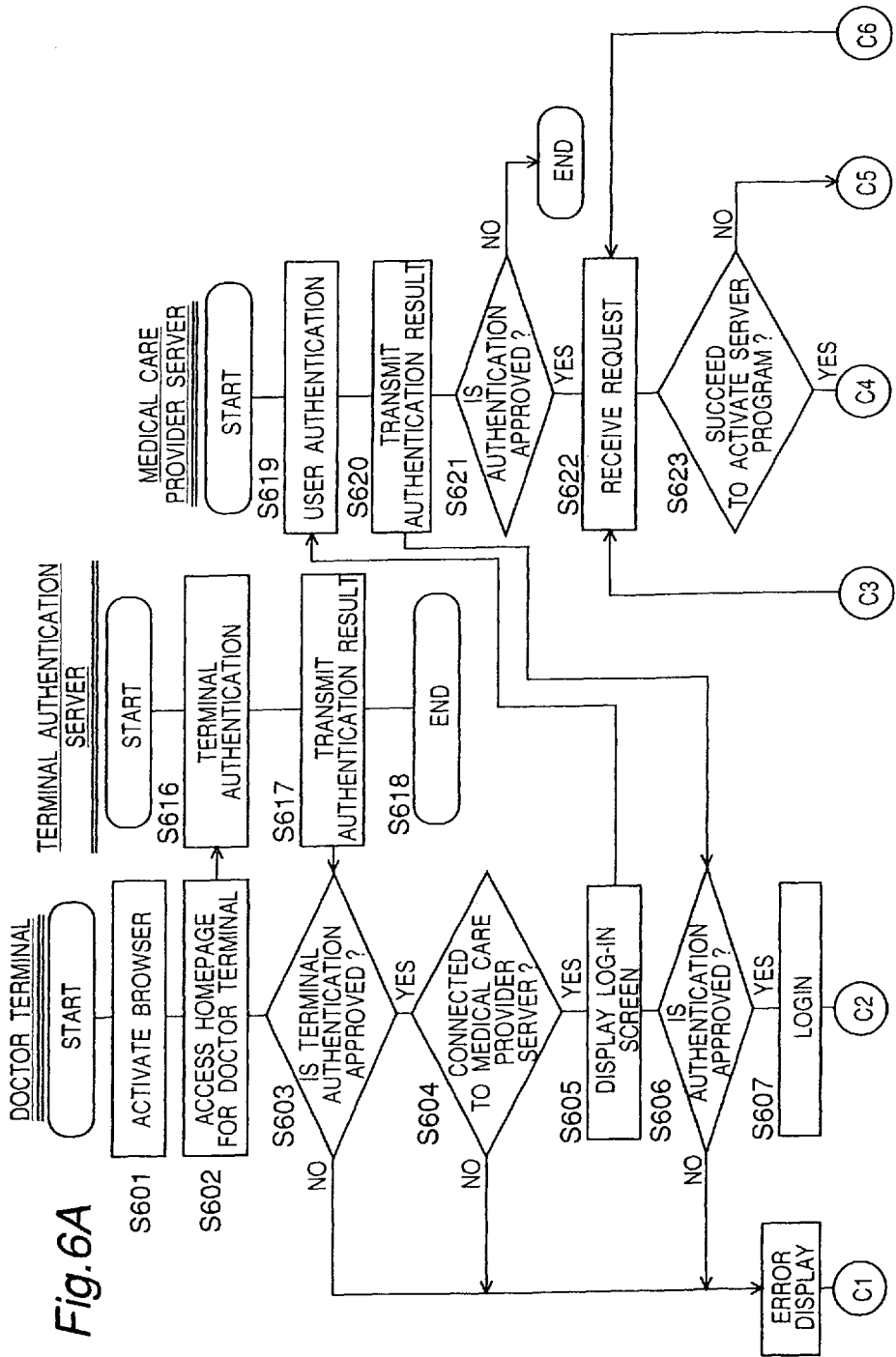
FIGS. 6A and 6B are respectively a flow chart for explaining browsing of the vital data retained in the medical care provider server by a doctor terminal.
Figure 6B:
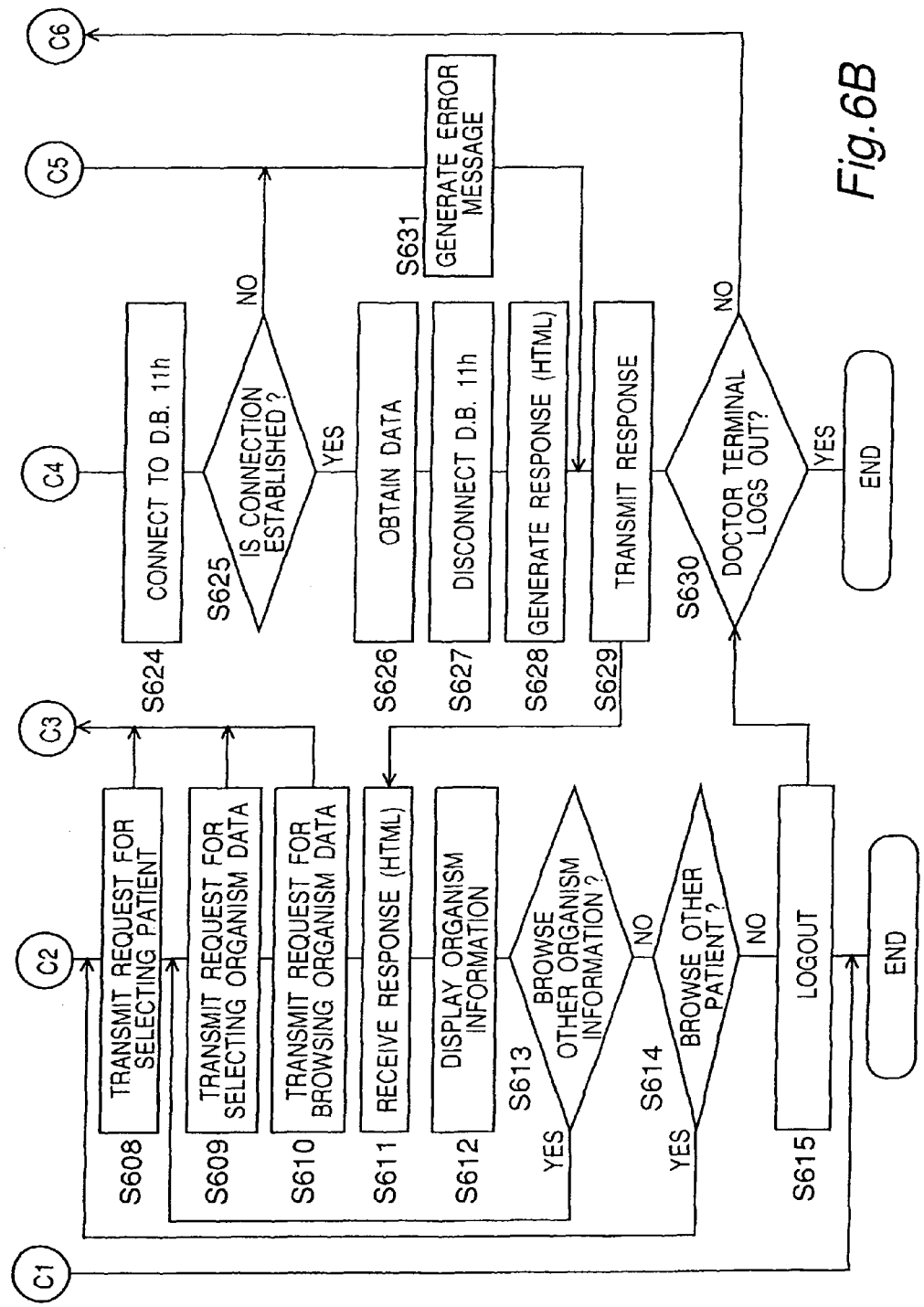

Browsing of the vital information stored in the medical care provider server by the doctor terminal 5 will be described below with reference to FIGS. 6A and 6B.

The doctor terminal 5 activates browser software installed therein at step S601 and accesses a home page set up in the medical care provider server 2. The terminal authentication server 18 performs authentication of the doctor terminal 5 seeking the access at step S616 and transmits a result of the authentication to the doctor terminal 5 at step S617. It should be noted that the doctor terminal 5 has obtained certification issued by the terminal authentication terminal 18 in advance. Specifically, provided that the data regarding a particular doctor terminal is registered to a institution managing the medical information system such as a management center, the certification is (electronically) issued by the terminal authentication server 18 to the doctor terminal 5. By using identification data included in the certification and registered in the doctor terminal 5, the terminal authentication server 18 performs the authentication when the doctor terminal 5 tries to access the home page. Alternatively, by using the certification (electronically) issued by the terminal authentication server 18 and introduced to the doctor terminal 5 through a medium that is not duplicable (e.g. floppy disk, IC card, or onetime password generator), the terminal authentication server 18 performs the authentication when the doctor terminal tries to access.

In the case where the authentication has been approved at step S606 and that the connection to the medial care provider server is determined to be possible at step S604, a login screen is displayed at step S605. Then, the medical care provider server 2 performs authentication of the doctor terminal 5 requiring the login at step S619 and transmits a result of the authentication to the doctor terminal 5 at step S620. If the authentication has been approved at step S606, the doctor terminal 5 logs in to the server. Further, the doctor terminal 5 transmits to the medical care provider server 2 a request for selecting a patient whose information is sought to be browsed at step S608 and a request for selecting vital data that is required to be browsed at step S609. Then, the doctor terminal 5 transmits a request for browsing the vital data to the medical care provider server 2 at step S610.

The medical care provider server 2 receives these requests at step S622. If activation of the server program 11*e* has succeeded at step S624, then the care medical care provider server 2 performs connection to the database files 11*h*. If the connection to the database files 11*h* has succeeded at the step S625, the medical care provider server 2 obtains the vital data corresponding to the requests from the doctor terminal 5 (steps S608 and S609) and then disconnects the connection to the database files 11*h*. On the other hand, in the case where the activation of the server program 11*e* has not succeeded at step S623 or the connection to the database files 11*h* is determined to be impossible at step S625, an error message is generated at step S631.

Further, the medical care provider server 2 creates a response to the doctor terminal 5 in HTML format at step S628 and transmits the response to the doctor terminal 5 at step S629. The response includes the requested vital information or the error message. Unless the doctor terminal 5 loges out at step S630, the medical care provider server continues to perform processes after step S622.

Figure 7A:
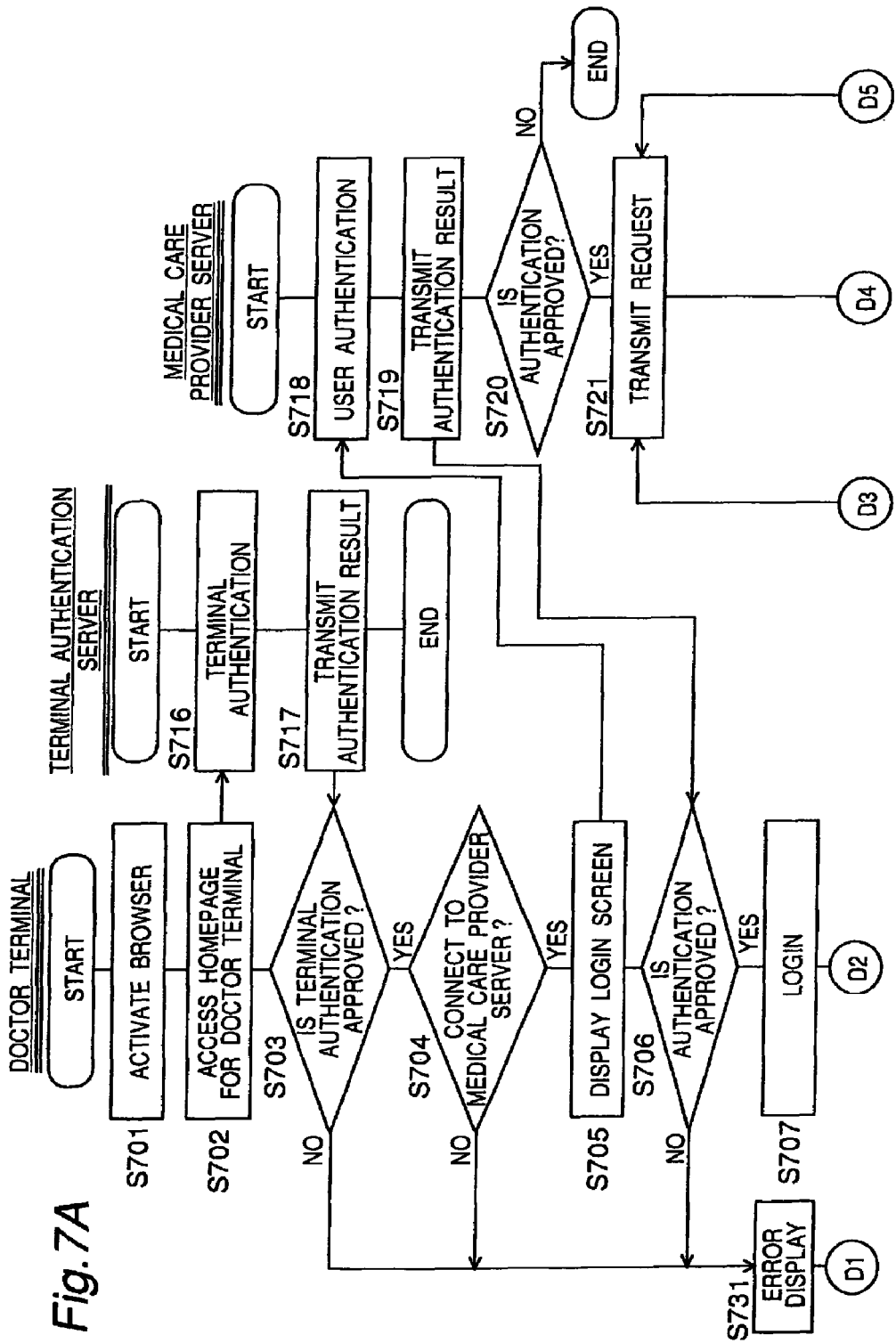
FIGS. 7A and 7B are respectively a flow chart for explaining transmission of a medical inquiry from the doctor terminal to the medical care provider server.
Figure 7B:
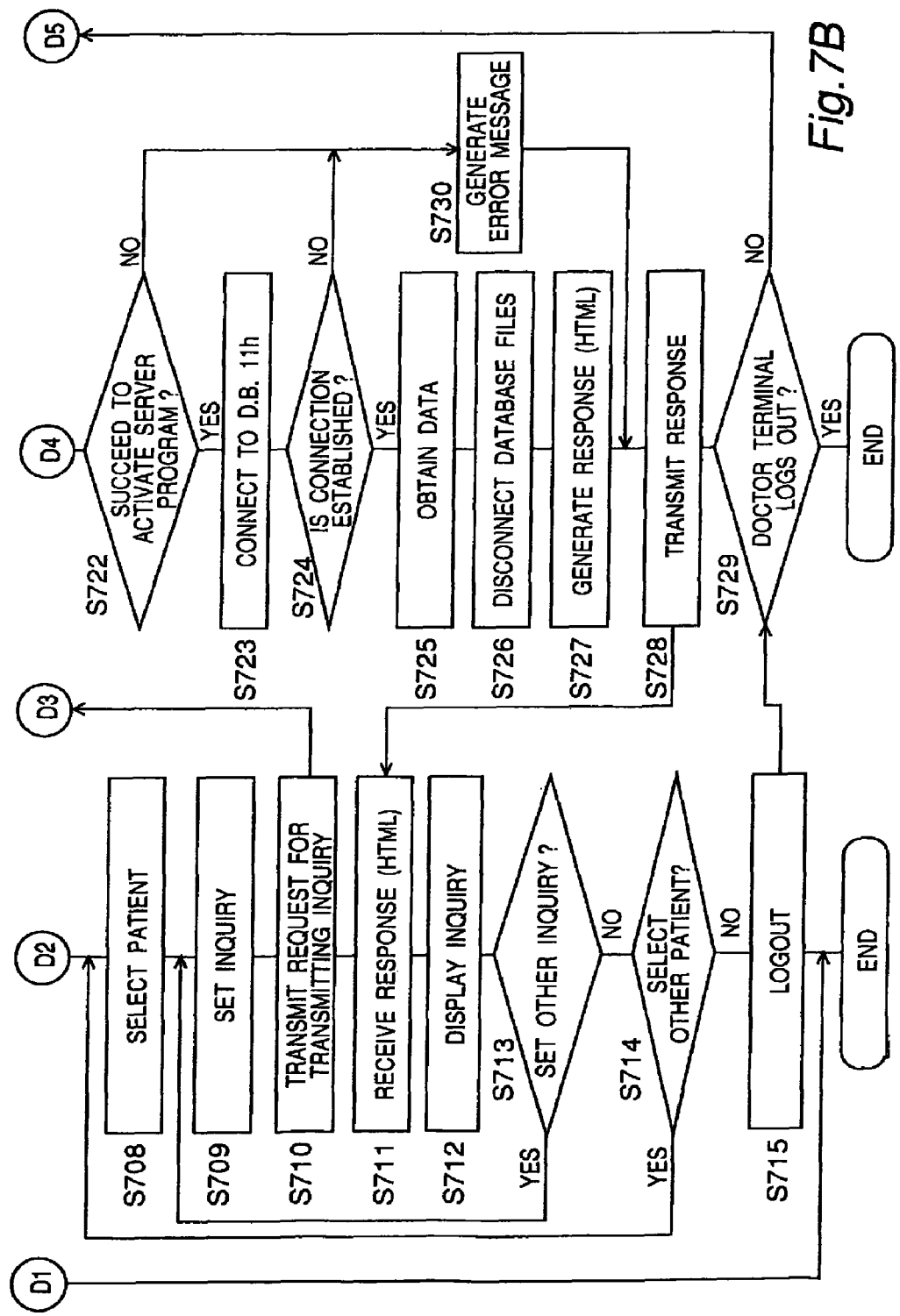

Next, transmission of the inquiry from the doctor terminal 5 to the medical care provider server 2 will be described with reference to FIGS. 7A and 7B. First, the doctor terminal 5 activates browser software installed therein at step S701 and accesses the home page for the doctor terminals at step S702. The terminal authentication server 18 performs authentication of the doctor terminal 5 seeking the access at step 716, and then transmits a result of the authentication to the doctor terminal 5 at step S717. In the case where the authentication has been approved at step S703 and the connection to the medical care provider server 2 is determined to be possible at step S704, the login screen is displayed at step S705. Then, the medical care provider server 2 performs authentication of the doctor terminal 5 requiring the login at step S718 and transmits a result of the authentication to the doctor terminal 5 at step S620. It should be noted that the doctor terminal 5 has obtained certification issued (electronically) by the terminal authentication server 18 in advance as well as certification enabling the doctor terminal 5 to browse the vital data. If the authentication has been approved at step S706, the doctor terminal 5 logs in to the server at step S707. Further, selection of a patient to whom the inquiry is to be sent is performed at step S708, and then setting of contents of the medical inquiry is performed at step S709. The contents of medical inquiry include items such as whether or not a patient is taking meals or a patient's sleeping time. However, the contents of the inquiry are not limited to these. The doctor who is the user of the doctor terminal 5 can set the contents depending on a particular user who is the user of the patient terminal 1 and his or her medical condition. Then, a request for transmitting the medical inquiry is transmitted from the doctor terminal 5 to the medical care provider server 2 at step S710.

The medical care provider server 2 receives the request for transmitting the medical inquiry at step S721 and if activation of the server program 11*e* has succeeded at step S722, then the medical care provider server 2 performs connection to the database files 11*h* at step S723. If the connection to the database files 11*h* has succeeded at step S724, then the medical care provider server 2 stores the data of the medical inquiry transmitted from the doctor terminal 5 in the database files 11*h*, followed by disconnecting the connection to the database files 11*h* at step S726. On the other hand, in the case where the activation of the server program 11*e* has not succeeded at step S722 or the connection to the database files 11*h* is determined to be impossible at step S625, an error message is generated at step S730.

Further, the medical care provider server 2 creates a response to the doctor terminal 5 in HTML format at step S727 and transmits the response to the doctor terminal 5 at step S728. The response includes the contents of the inquiry received from the doctor terminal 5 or the error message. After the doctor terminal 5 receives the response at step S711, the inquiry is displayed at step S712. If another inquiry is to be set at step S713, then the processes after step S709 are repeated. If another patient is to be selected at step S714, then the processes after step S708 are repeated. Unless the doctor terminal 5 has logged out at step S729, the processes after step S721 are repeated.

Figure 8A:
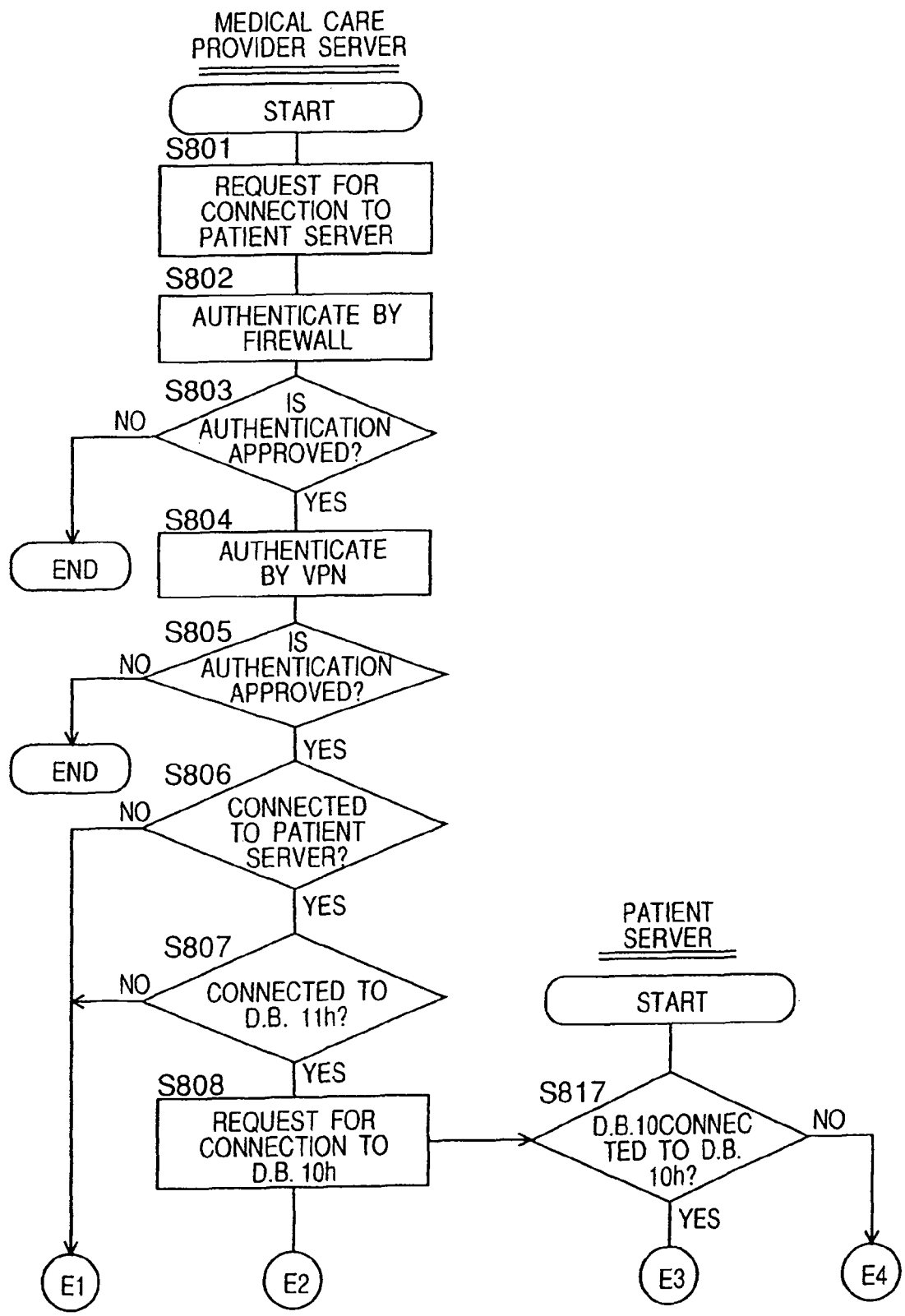
FIGS. 8A and 8B are respectively a flow chart for explaining transmission of the medical inquiry from the medical care provider server to the patient server.
Figure 8B:
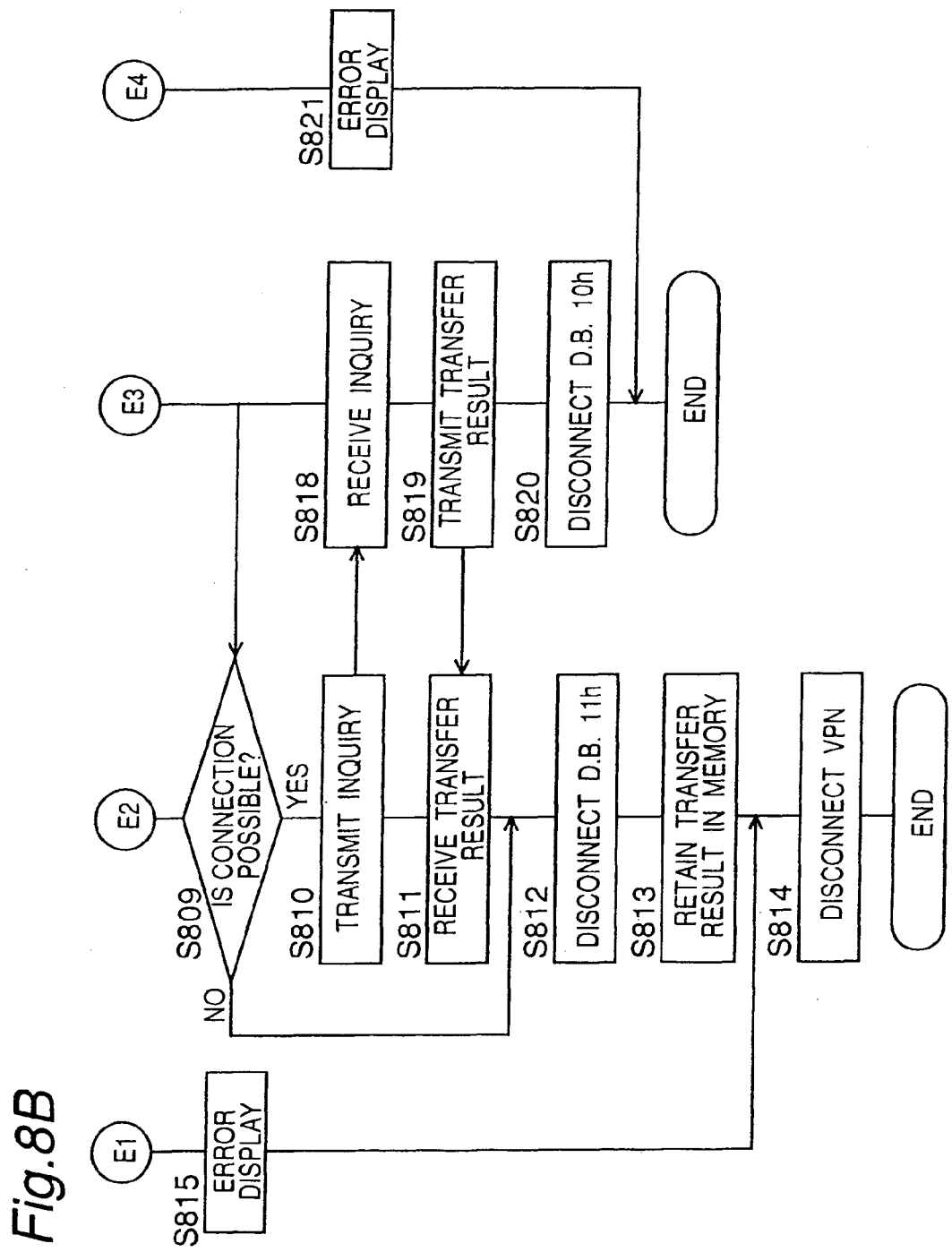

FIGS. 8A and 8B illustrate processes that are performed until the inquiry is transmitted from the medical care provider server 2 to the patient server 1. Subsequent to the transmission of a connection request from the medical care provider server 2 to the patient server 1 at step S801, the firewall 12A for the patient server 1 performs authentication at step S802. If the authentication by the firewall 12A has been approved at step S803, then the VPN 13A for the patient server 1 performs further authentication at step S804. In the case where the authentication by the VPN 13A has been approved at step S805, connection to the patient server 1 is determined to be possible at step S806, and it is determined that the medical care provider server 2 can connect to the database files 11*h* thereof at step S807, the medical care provider server 2 requests the patient server 1 to connect to the database files 10*h* at step S808. On the other hand, in the case where the connection to the patient server 1 is determined to be impossible at step S806 or the connection to the database files 11*h* is determined to be impossible at step S807, the medical care provider server 2 performs the error display at step S815.

If the patient server 1 has been connected to the database files 10*h* at steps S817 and S809, then the medical care provider server 2 transmits the inquiry to the patient server 1 at step S810. The patient server 1 receives the inquiry and then stores the inquiry in the database files 10*h* at step S818. Further, after transmitting a transfer result to the medical care provider server 2 at step S819, the patient server 1 disconnects the connection to the database files 10*h*. On the other hand, if the connection to the database files 10*h* is denied at step S817, then the patient server performs the error display at step S821.

After receiving the transfer result from the patient server 1 at step S811, the medical care provider server 2 disconnects the connection to the database files 11*h* at step S812. Then, the medical care provider server 2 retains the transfer result in the memory at step S813 and disconnects the connection to the VPN 13A at step S814.

Figure 9A:
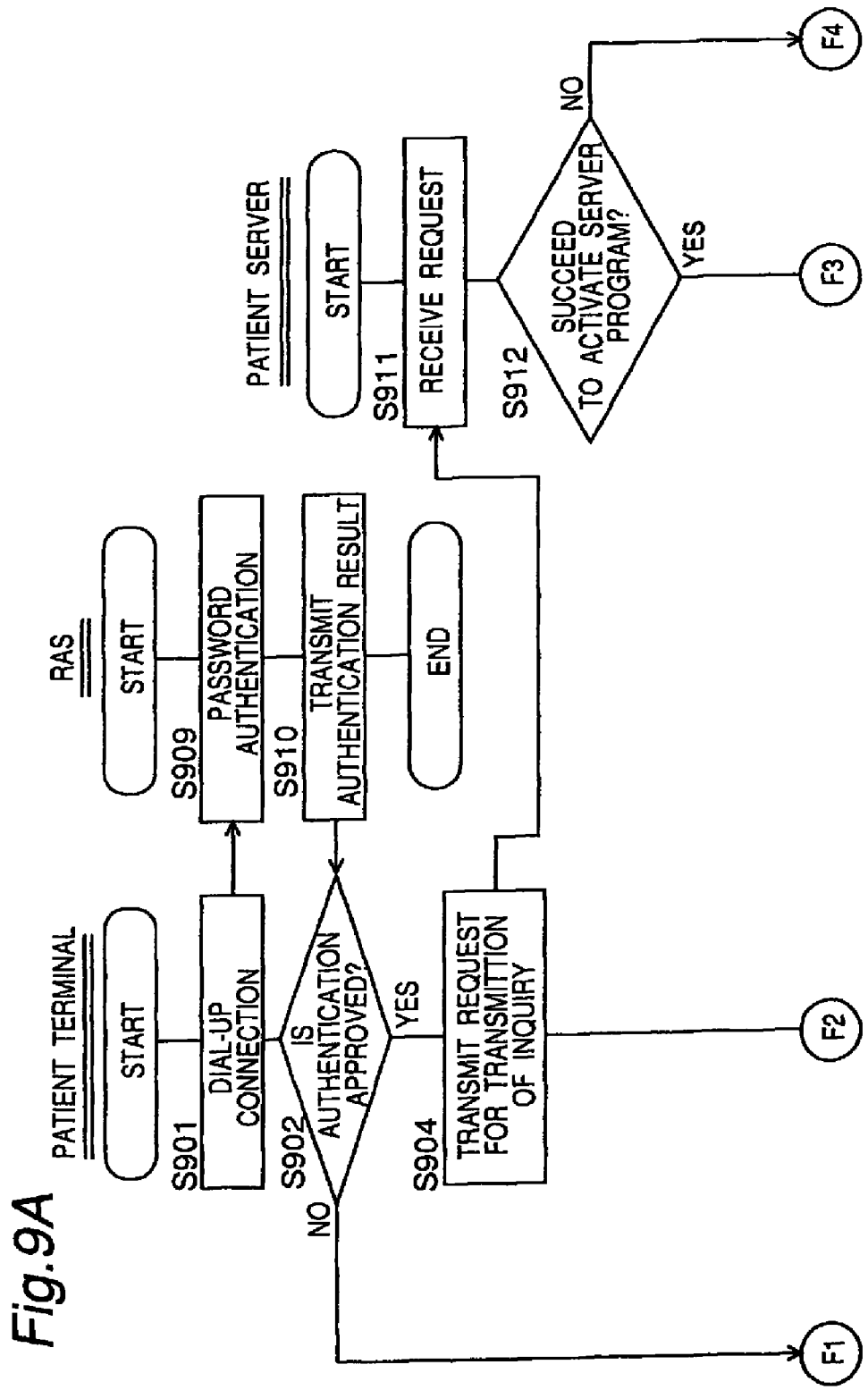
FIGS. 9A and 9B are respectively a flow chart for explaining transmission of a reply to the medical inquiry from the patient server to the patient terminal.
Figure 9B:
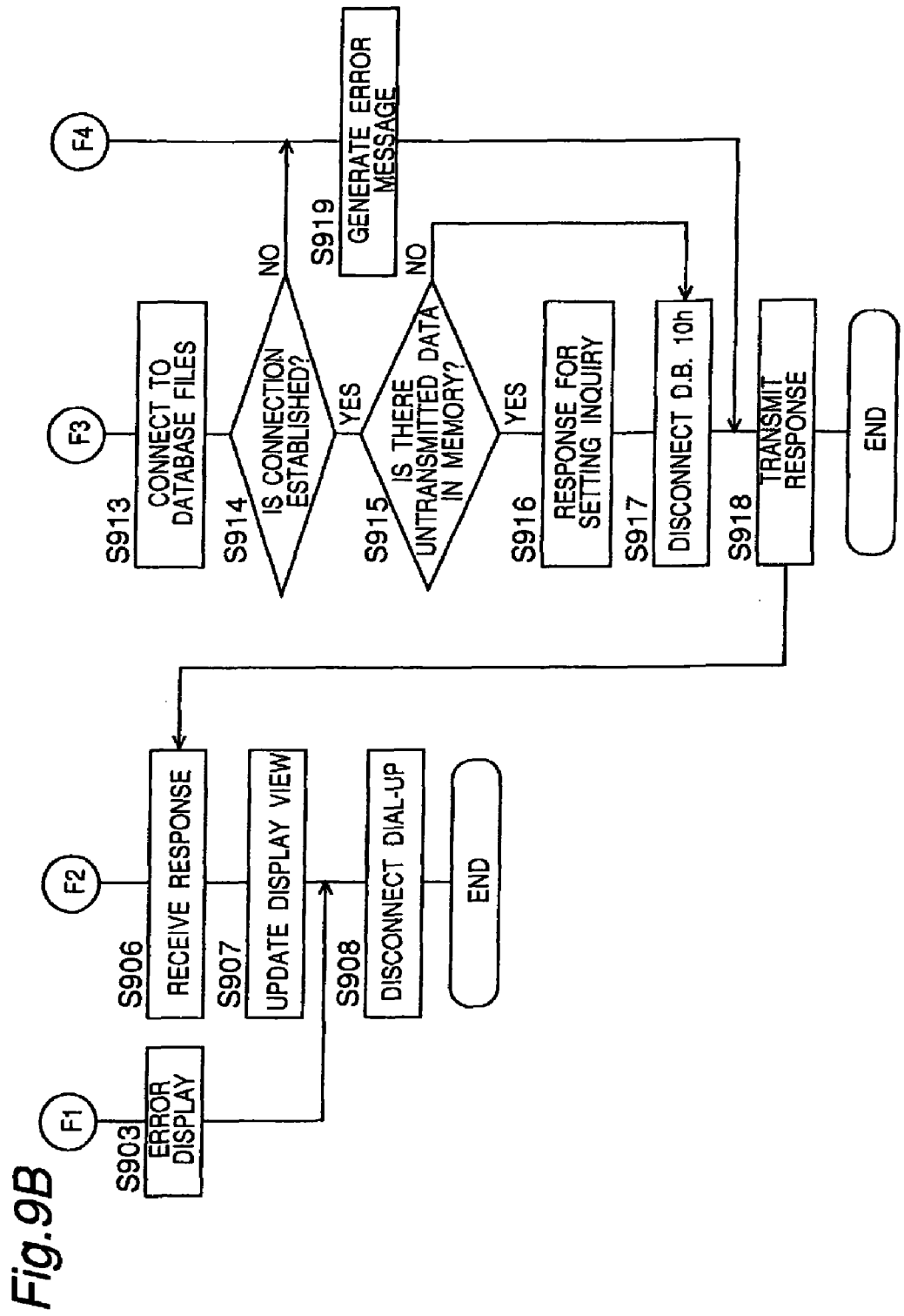

Next, transmission of the inquiry from the patient server 1 to the patient terminal will be described with reference to FIGS. 9A and 9B.

First, at step S901, the patient terminal 4 requires access to the RAS 15 by means of dial-up connection through the phone line 14. The RAS 15 performs authentication of the patient terminal 4 requiring the access by means of a password at step S909, and transmits a result of the authentication to the patient terminal 4 at step S910. If the authentication has been denied at step S902, then the patient server 4 performs an error display at step S903 and disconnects the dial-up connection at step S908. On the other hand, if the authentication has been approved at step S902, then the patient terminal 4 transmits a request for transmission of the medical inquiry to the patient server 1 at step S904. After receiving the request at step S911, in the case where activation of the server program 10*e* has succeeded at step S912, the patient server 1 performs connection to the database files 10*h* at step S913. Further, in the case where connection to the database files 10*h* has succeeded at step S914, the patient server 1 checks whether or not there exists any data that has not yet been transmitted at step S915.

In the case where the inquiry not transmitted to the patient terminal 4 exists, the patient server 1 creates a response for setting the inquiry and then disconnects the connection to the database files 10*h*. On the other hand, in the case where the server program 10*h* has not been activated at step S912 or the connection to the database files 10*h* is determined to be impossible at step S914, the patient server 4 creates an error message.

The patient terminal 4 receives the response to retain in the memory at step S906. After updating the screen display at step S907, the patient terminal 4 disconnects the dial-up connection at step S908.

FIG. 10 illustrates an example of structures of the data stored in the database files 10*h*. Although body weights of patients and whether or not the patients are taking meals are shown in this example, the vital data and the medical inquiry are not limited to these items. As shown in FIG. 10, the patient server 1 stores the vital data for each unique ID that is respectively allocated to a particular patient who is an user of the patient terminal 4. Further, transmission flags in FIG. 10 include information relating to whether or not transfer of the measurement data and the reply to the medical inquiry has been finished. Specifically, a value of "0" for the transmission flag indicates that corresponding data, which is the vital data or the reply to the medical inquiry, has not been finished yet, whereas a value of "1" for the transmission flag indicates that the transfer has been already finished. Concretely, when the transmission of one measurement value (body weight), e.g. "65.75", is finished at step S511 in FIG. 6, a transmission flag corresponding to the measurement value (body weight) is changed from "0" to "1". This control of the transmission flag allows the system administrator of the patient server 1 to delete measurement data and the replies having the transmission flag of "1" in the data retained in the patient server 1, thereby resulting in simplification of maintenance of the database.

On the other hand, FIG. 11 illustrates an example of structures of the data stored in database files 11*h* of the medical care provider server 2. Similar to the data structure of the patient server 1, the vital data is stored for each unique ID that is respectively allocated to a particular patient. Patient data is also stored for each of IDs. The patient data includes information for identifying a particular patient such as name. It should be noted that the transmission flag in FIG. 11 has the same function as that of the transmission flag in FIG. 10.

As described above, although the patient server 1 stores the vital data for each of the IDs, the patient server 1 does not store the patient data corresponding to each of the IDs. Accordingly, if the patient server 1 were accessed without authorization, it would be impossible to identify each of the vital data of a particular patient.

In the medical information system according to the first embodiment of the invention, the patient server 1 processes collecting of the vital information from the patient terminals 4, whereas the medical care provider server 2 processes browsing of the vital information by the doctor terminals 5. In other words, in the medical information system, the processes are decentralized by concurrent processes in the patient server 1 and the medical care provider server 2, thereby reducing loads to the respect servers. Thus, response time is reduced, resulting in an improvement of communication speed. Further, stability of the system is improved by reducing the loads to the patient server 2 and the medical care provider server 3. This enables the collection of the vital information from the patient terminal 4 and the browsing of the vital information by the doctor terminal 5 to always be executed in a stable manner.

The patient terminal 4 is connected to the patient server 1, whereas the doctor terminal 5 is connected to the medical care provider server 2. Accordingly, when a server program is modified so as to adapt the program to changes in specification or the addition of a patient terminal 4, only the patient server 1 needs to be downed, whereas the browsing of the vital information retained in the medical care provider server 2 by the doctor terminal 5 can be continued. Conversely, when the server program is modified so as to adapt the program to changes in specification or the addition of a doctor terminal 5, only the medical care provider server 2 needs to be downed, whereas the collection of the vital information by the patient server 1 can be continued.

Operation and management of the patient server 1 by the system administrator holding it simplify the maintenance and operation of the data. On the other hand, the medical institute holding the medical care provider server 2 can use the vital information retained in the medical care provider server 2 for other medical information systems such as the electronic chart system. As a result, the medical information system according to the first embodiment has high flexibility.

The patient server 1 only can be accessed directly from the patient terminal 4 through the second network 3B. Further, the combination of the firewalls 12A, 12B and VPNs 13A, 13B provided in the first network 3A has a higher security level than that of the RAS 15 provided in the second network 3B. Accordingly, unauthorized access from the patient terminal 4 to the vital information retained in the medical care provider server 2 can be prevented. Also, the lower security level of the RAS 15 provided in the second network 3B than those of the combination of the firewalls 12A, 12B and the VPNs 13A, 13B provided in the second network 3B and the terminal authentication server 18 provided in the third network 3C ensures a convenient connection from the patient terminal 4 to the patient server 1. The high security level of the third network 3C connecting the doctor terminal 5 and the medical care provider server 2 to each other prevents unauthorized access directly to the medical care provider server 2. As a result, the medical information system according to the first embodiment has a very high level of security.

Second Embodiment

Figure 12:
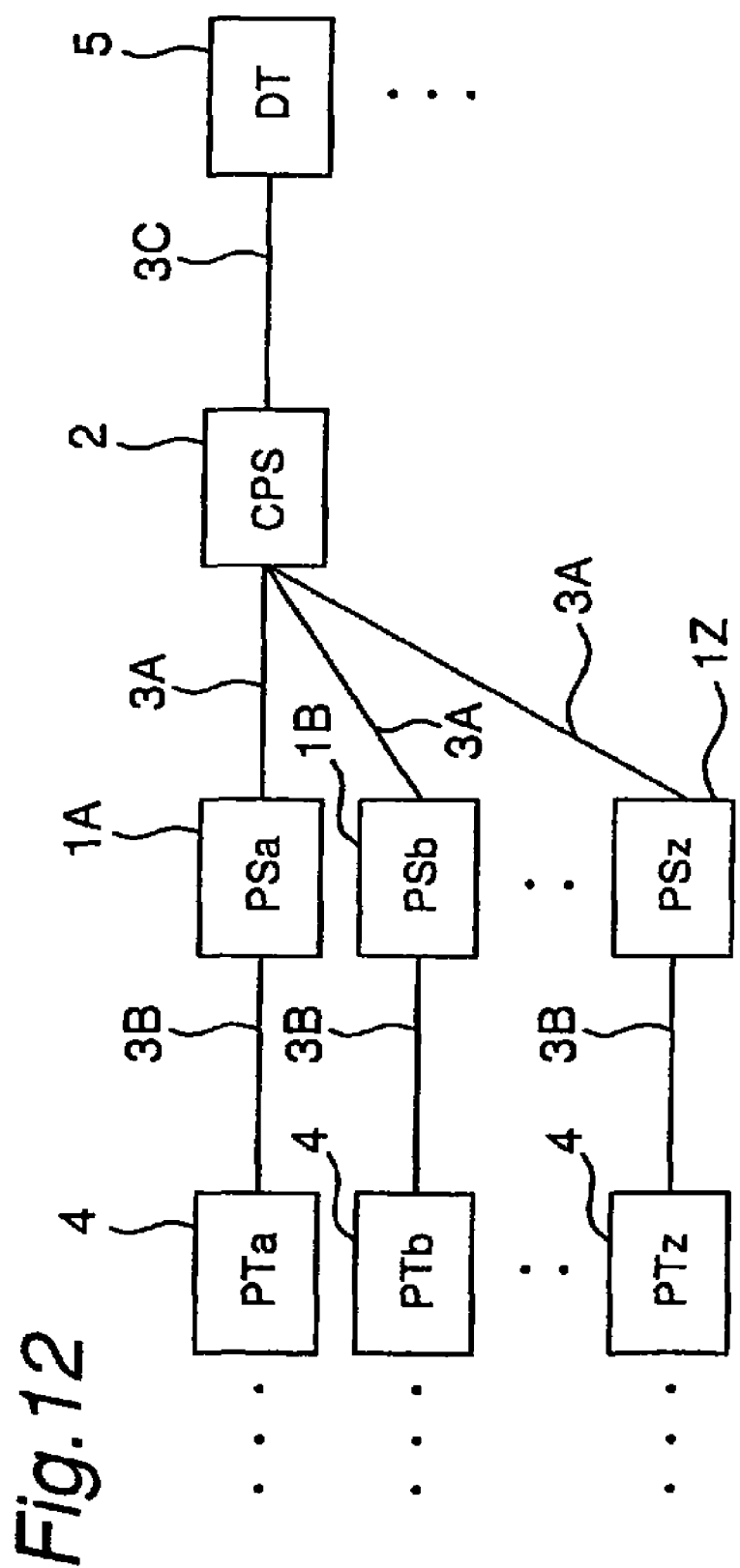
FIG. 12 is a schematic block diagram showing a medical information system according to a second embodiment of the present invention.

FIG. 12 is a schematic view showing a second embodiment of the present invention.

In this second embodiment, a plurality of patient servers 1A, 1B, . . . , 1Z are provided. Further, each of the patient servers 1A, 1B, . . . , 1Z is connected to the medical care provider server 2 through the first network 3A. Furthermore, to each of the patient servers 1A, 1B, . . . , 1Z, a plurality of patient terminals 4 are connected. Due to the provision of the plurality of patient servers 1A, 1B, . . . , 1Z, when a server program is modified so as to adapt the program to change in specification or the addition of patient terminals connected to one of the patient servers 1A, 1B, . . . 1Z, only the corresponding patient server needs to be downed. The other patient servers can continue to collect the vital information from the patient terminals connected thereto.

Further, in the system according to the second embodiment, where a different type of patient terminals 4 (concretely, patient terminals using different type of communication protocols for communication with the patient server) is introduced for collection of the measurement data and the reply to the medical inquiry, the new patient terminals and corresponding patient server can be introduced with continuing management of the existing system.

Since other constructions and operations of the second embodiment are the same as those of the first embodiment, a description is unnecessary by allocating the same reference numerals to the same elements.

Third Embodiment

Figure 13:
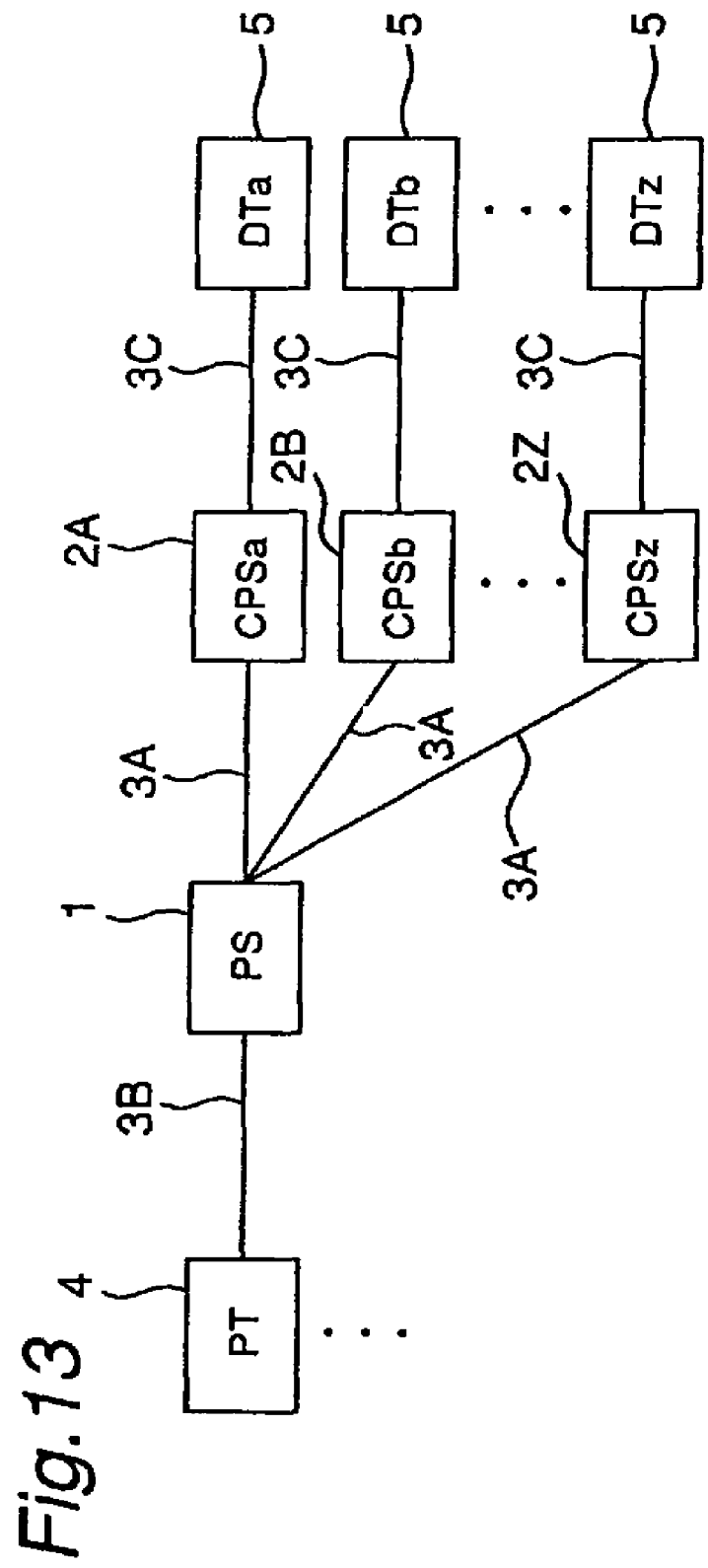
FIG. 13 is a schematic block diagram showing a medical information system according to a third embodiment of the present invention.

FIG. 13 illustrates a third embodiment of the present invention.

Figure 14:
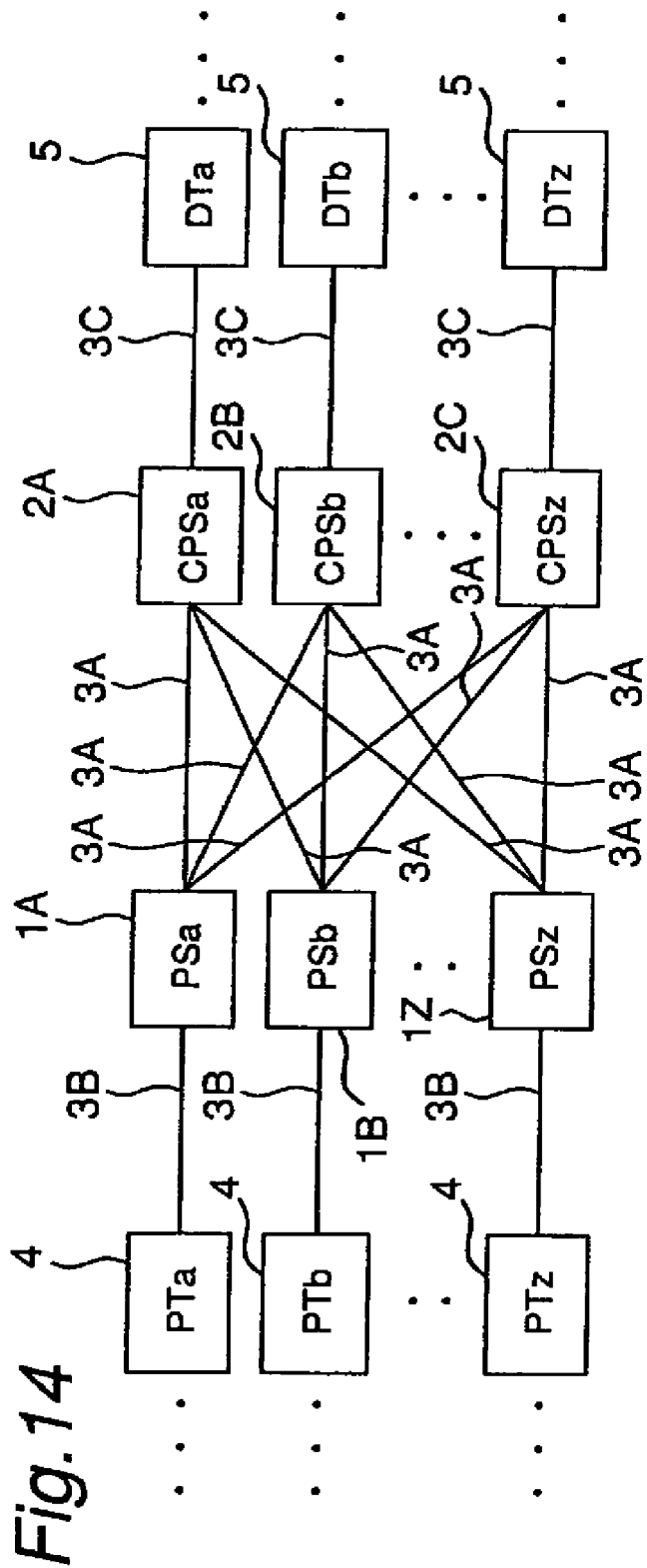
FIG. 14 is a schematic block diagram showing a medical information system according to a fourth embodiment of the present invention.

In the third embodiment, a plurality of medical care provider servers 2A, 2B, . . . , 2Z are provided. Further, the patient server 1 is connected to the medical care provider servers 2A, 2B, . . . , 2Z through the first network 3A. Furthermore, a plurality of doctor terminals 5 are connected to each of the medical care provider servers 2A, 2B, . . . , 2Z. Each of the medical care provider servers 2A, 2B, . . . , 2Z can be held and managed by corresponding medical institutes. Accordingly, each of the medical institutes can retain the vital information in the medical care provider server for a long time according to their demand. Further, views at doctor terminals 5 when the vital information is browsed can be customized in accordance with each of the medical institutes. As shown in FIG. 14, a plurality of patient servers 1 and a plurality of medical care provider servers 2 may be provided.

Since other constructions and operations of the third embodiment are the same as those of the first embodiment, a description is unnecessary by allocating same reference numerals to the same elements.

Fourth Embodiment

Figure 15:
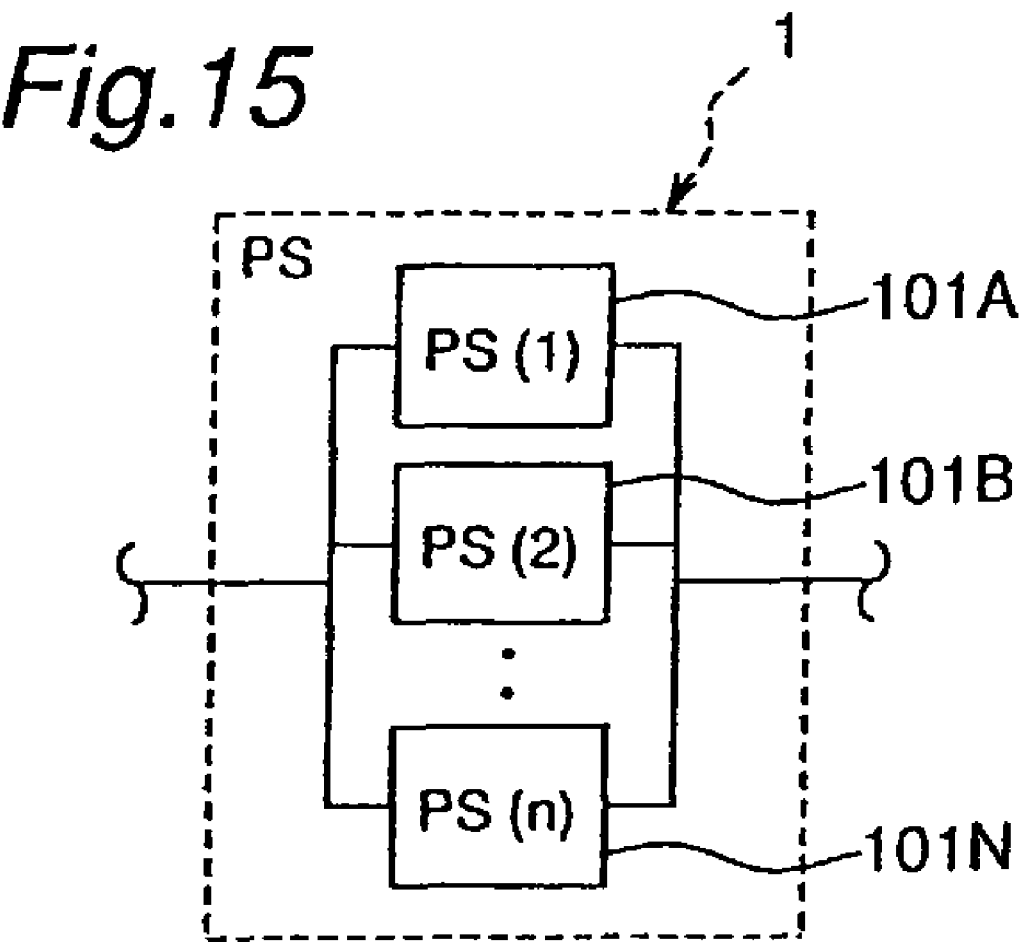
FIG. 15 is a schematic block diagram showing an example of a clustered patient server.

As shown in FIG. 15, in a fourth embodiment of the present invention, the patient server 1 is clustered. Specifically, the patient server 1 consists of a plurality of servers 101A, 101B, . . . , 101Z provided in parallel, and appears as a single of server when accessed by the patient terminal 4 or medical care provider server 2. This kind of construction is refereed to as clustering. This clustering enables the load to each server to be further decentralized. Due to the parallel arrangement of the servers, if the server 101A is downed, for example, the system can continue to be operated by the remaining servers 101B, . . . , 101N. This improves fault tolerance and makes it possible to realize a system that remains operable 24 hours a day.

It should be noted that while the description about the clustering is made with reference the patient server 1 as a example in this embodiment, the clustering can also be adopted to the medical care provider server 2.

Although the present invention has been fully described by way of the examples with reference to the accompanying drawings, it is to be noted here that various changes and modifications will be apparent to those who are skilled in the art. Therefore, unless such changes and modifications otherwise depart from the spirit and scope of the present invention, they should be construed as being included therein.

What is claimed is:

1. A medical information system comprising:
 a patient server comprising a first database, said patient server receiving vital information and unique identifications allocated to patients, storing and managing the received vital information and unique identifications in said first database such that the vital information is associated with a corresponding unique identification, and such that correspondence between each of the unique identifications and patient data, wherein the patient data includes at least a patient name, is unrecognizable, and transmitting the stored and managed vital information and unique identifications;

a medical care provider server connected to said patient server through a first network and comprising a second database, said medical care provider server receiving the vital information and unique identifications from said first database of said patient server through the first network, storing and managing the received vital information, unique identifications, and patient data in said second database, associate each of the unique identifications with corresponding patient data, identifying corresponding patient data using each of the unique identifications, and allowing the stored and managed vital information, unique identifications, and patient data to be browsed;

a patient terminal connected to said patient server through a second network, said patient terminal transmitting the vital information and unique identifications to said patient server through the second network; and a doctor terminal connected to said medical care provider server through a third network, said doctor terminal browsing the vital information, unique identifications, and patient data stored and managed in said medical care provider server through the third network, wherein the first network is configured to allow communication between said patient server and said medical care provider server and disallow communication between either said patient terminal or said doctor terminal and either said patient server or said medical care provider server, and disallow communication between said patient terminal and said doctor terminal, wherein the second network is configured to allow communication between said patient terminal and said patient server, and disallow communication among said patient server, said medical care provider server, and said doctor terminal, and wherein the third network is configured to allow communication between said doctor terminal and said medical care provider server, and disallow communication among said patient server, said medical care provider server, and said patient terminal.

2. A medical information system according to claim 1, further comprising a sensor for measuring vital data, wherein the vital information includes a measurement value by said sensor.

3. A medical information system according to claim 1, wherein:

said doctor terminal transmits, as consultation data, an inquiry regarding a health status of a patient to said medical care provider server through the third network; and the vital information transmitted from said patient terminal to said patient server through the second network includes a reply to the inquiry transmitted to said patient terminal.

4. A medical information system according to claim 1, further comprising:

a first unauthorized access prevention section provided in the first network;

a second unauthorized access prevention section provided in the second network; and a third unauthorized access prevention section provided in the third network, wherein said first and third unauthorized access prevention sections have higher security levels than a security level of said second unauthorized access prevention section.

5. A medical information system according to claim 4, wherein:

said first unauthorized access prevention section comprises a firewall and a virtual private network;

said second unauthorized access prevention section comprises a remote access server; and said third unauthorized access prevention section comprises a terminal authentication server.

6. A medical information system according to claim 1, wherein said patient server and said medical care provider server are respectively clustered.

7. A medical information system comprising:

a plurality of patient servers each comprising a first database and each patient server receiving vital information and unique identifications allocated to patients, storing and managing the received vital information and unique identifications in a respective first database such that the vital information is associated with a corresponding unique identification, and such that correspondence between each of the unique identifications and patient data, wherein the patient data includes at least a patient name, is unrecognizable, and transmitting the stored and managed vital information and unique identifications;

a medical care provider server connected to said plurality of patient servers through a first network and comprising a second database, said medical care provider server receiving the vital information and unique identifications from each of said first databases of said plurality of patient servers through the first network, storing and managing the received vital information, unique identifications, and patient data, associate each of the unique identifications with corresponding patient data, identifying the corresponding patient data using each of the unique identifications, and allowing the stored and managed vital information, unique identifications, and patient data to be browsed;

a plurality of patient terminals each connected to at least one of said patient servers through a second network, said patient terminals respectively transmit the vital information and unique identifications to said patient servers through the second network; and a doctor terminal connected to said medical care provider server through a third network, said doctor terminal browsing the vital information, unique identifications, and patient data stored and managed in said medical care provider server through the third network, wherein the first network is configured to allow communication between said patient servers and said medical care provider server and disallow communication between either said patient terminals or said doctor terminal and either said patient servers or said medical care provider server, and disallow communication between said patient terminals and said doctor terminal, wherein the second network is configured to allow communication between said patient terminals and said patient servers, and disallow communication among said patient servers, said medical care provider server, and said doctor terminal, and wherein the third network is configured to allow communication between said doctor terminal and said medical care provider server, and disallow communication among said patient servers, said medical care provider server, and said patient terminals.

8. A medical information system according to claim 7, wherein each of said plurality of patient terminals includes a sensor for measuring vital data, and the vital information includes a measurement value by said sensor.

9. A medical information system according to claim 7, wherein:
   said doctor terminal transmits, as consultation data, an inquiry regarding a health status of a patient to said medical care provider server through the third network; and
   the vital information transmitted from one of said patient terminals to a corresponding patient server through the second network includes a reply to the inquiry transmitted to said one of said patient terminals.

10. A medical information system according to claim 7, further comprising:
   a first unauthorized access prevention section provided in the first network;
   a second unauthorized access prevention section provided in the second network; and
   a third unauthorized access prevention section provided in the third network,
   wherein said first and third unauthorized access prevention sections have higher security levels than a security level of said second unauthorized access prevention section.

11. A medical information system according to claim 10, wherein:
   said first unauthorized access prevention section comprises a firewall and a virtual private network;
   said second unauthorized access prevention section comprises a remote access server; and
   said third unauthorized access prevention section comprises a terminal authentication server.

12. A medical information system comprising:
   a patient server comprising a first database, said patient server receiving vital information and unique identifications allocated to patients, storing and managing the received vital information and said unique identifications such that the vital information is associated with a corresponding unique identification, and such that correspondence between each of the unique identifications and patient data, wherein the patient data includes at least a patient name, is unrecognizable, and transmitting the stored and managed vital information and unique identifications;
   a plurality of medical care provider servers connected to said patient server through a first network and each comprising a second database, said medical care provider servers respectively receiving the vital information and unique identifications from said patient server through the first network, storing and managing the received vital information, unique identifications and patient data in said second database, associate each of the unique identifications with corresponding patient data, identify corresponding patient data using each of the unique identifications, and allowing the stored and managed vital information, unique identifications, and patient data to be browsed;
   a patient terminal connected to said patient server through a second network, said patient terminal transmitting the vital information and unique identifications to said patient server through the second network; and
   a plurality of doctor terminals each connected to at least one of said medical care provider servers through a third network, said plurality of doctor terminals browsing the vital information, unique identifications, and patient data stored and managed in said medical care provider servers through the third network, respectively,
   wherein the first network is configured to allow communication between said patient server and said medical care provider servers and disallow communication between either said patient terminal or said doctor terminals and either said patient server or said medical care provider servers, and disallow communication between said patient terminal and said doctor terminals,
   wherein the second network is configured to allow communication between said patient terminal and said patient server, and disallow communication among said patient server, said medical care provider servers, and said doctor terminals, and
   wherein the third network is configured to allow communication between said doctor terminals and said medical care provider servers, and disallow communication among said patient server, said medical care provider servers, and said patient terminal.

13. A medical information system according to claim 12, wherein said patient terminal includes a sensor for measuring vital data, and the vital information includes a measurement value by said sensor.

14. A medical information system according to claim 12, wherein:
   each of said plurality of doctor terminals transmits, as consultation data, an inquiry regarding a health status of a patient through the third network to a respective one of said plurality of medical care provider servers; and
   the vital information transmitted from said patient terminal to said patient server through the second network includes a reply to the inquiry transmitted to said patient terminal.

15. A medical information system according to claim 12, further comprising:
   a first unauthorized access prevention section provided in the first network;
   a second unauthorized access prevention section provided in the second network; and
   a third unauthorized access prevention section provided in the third network,
   wherein said first and third unauthorized access prevention sections have higher security levels than a security level of said second unauthorized access prevention section.

16. A medical information system according to claim 15, wherein:
   said first unauthorized access prevention section comprises a firewall and a virtual private network;
   said second unauthorized access prevention section comprises a remote access server; and
   said third unauthorized access prevention section comprises a terminal authentication server.

* * * * *